US012202950B2

(12) United States Patent
Berti et al.

(10) Patent No.: US 12,202,950 B2
(45) Date of Patent: *Jan. 21, 2025

(54) CATALYST-FREE SURFACE FUNCTIONALIZATION AND POLYMER GRAFTING

(71) Applicant: Illumina, Inc., San Diego, CA (US)

(72) Inventors: Lorenzo Berti, San Diego, CA (US); Andrew A. Brown, Cambridge (GB); Wayne N. George, Cambridge (GB)

(73) Assignee: Illumina, Inc., San Diego, CA (US)

(*) Notice: Subject to any disclaimer, the term of this patent is extended or adjusted under 35 U.S.C. 154(b) by 113 days.

This patent is subject to a terminal disclaimer.

(21) Appl. No.: 18/190,685

(22) Filed: Mar. 27, 2023

(65) Prior Publication Data

US 2023/0250248 A1 Aug. 10, 2023

Related U.S. Application Data

(60) Division of application No. 17/194,019, filed on Mar. 5, 2021, now Pat. No. 11,618,808, which is a continuation of application No. 15/989,079, filed on May 24, 2018, now Pat. No. 10,975,210, which is a continuation of application No. 14/316,478, filed on Jun. 26, 2014, now Pat. No. 9,994,687.

(60) Provisional application No. 61/971,381, filed on Mar. 27, 2014, provisional application No. 61/841,647, filed on Jul. 1, 2013.

(51) Int. Cl.

| C08J 7/12 | (2006.01) |
|---|---|
| B01J 19/00 | (2006.01) |
| C08F 8/00 | (2006.01) |
| C09D 133/26 | (2006.01) |
| C12Q 1/6837 | (2018.01) |
| C12Q 1/6874 | (2018.01) |
| C12Q 1/6876 | (2018.01) |
| C08F 220/60 | (2006.01) |

(52) U.S. Cl.
CPC ............. *C08J 7/12* (2013.01); *B01J 19/0046* (2013.01); *C08F 8/00* (2013.01); *C09D 133/26* (2013.01); *C12Q 1/6837* (2013.01); *C12Q 1/6874* (2013.01); *C12Q 1/6876* (2013.01); *B01J 2219/00529* (2013.01); *B01J 2219/00533* (2013.01); *B01J 2219/00619* (2013.01); *B01J 2219/00626* (2013.01); *B01J 2219/00637* (2013.01); *B01J 2219/00722* (2013.01); *C08F 220/603* (2020.02); *C08J 2335/00* (2013.01)

(58) Field of Classification Search
CPC ....................................................... C08J 7/12
See application file for complete search history.

(56) References Cited

U.S. PATENT DOCUMENTS

| 5,130,238 A | 7/1992 | Malek et al. |
|---|---|---|
| 5,429,807 A | 7/1995 | Matson et al. |
| 5,436,327 A | 7/1995 | Southern et al. |
| 5,455,166 A | 10/1995 | Walker |
| 5,561,071 A | 10/1996 | Hollenberg et al. |
| 5,583,211 A | 12/1996 | Coassin et al. |
| 5,599,675 A | 2/1997 | Brenner |
| 5,641,658 A | 6/1997 | Adams et al. |
| 5,658,734 A | 8/1997 | Brock et al. |
| 5,750,341 A | 5/1998 | Macevicz |
| 5,837,858 A | 11/1998 | Brennan |
| 5,874,219 A | 2/1999 | Rava et al. |
| 5,919,523 A | 7/1999 | Sundberg et al. |
| 6,136,269 A | 10/2000 | Winkler et al. |
| 6,210,891 B1 | 4/2001 | Nyren et al. |
| 6,214,587 B1 | 4/2001 | Dattagupta et al. |
| 6,258,568 B1 | 7/2001 | Nyren |
| 6,274,320 B1 | 8/2001 | Rothberg et al. |
| 6,287,768 B1 | 9/2001 | Chenchik et al. |
| 6,287,776 B1 | 9/2001 | Hefti |
| 6,288,220 B1 | 9/2001 | Kambara et al. |
| 6,291,193 B1 | 9/2001 | Khodadoust |
| 6,297,006 B1 | 10/2001 | Drmanac et al. |
| 6,346,413 B1 | 2/2002 | Fodor et al. |
| 6,355,431 B1 | 3/2002 | Chee et al. |
| 6,372,813 B1 | 4/2002 | Johnson et al. |

(Continued)

FOREIGN PATENT DOCUMENTS

| EP | 0 742 287 A2 | 11/1996 |
|---|---|---|
| EP | 0 799 897 A1 | 10/1997 |

(Continued)

OTHER PUBLICATIONS

Afonina, et al., "Efficient priming of PCR with short oligonucleotides conjugated to a minor groove binder". Nucleic Acids Research, 1997, vol. 25, No. 13 2657-2660.
Bains et al. (1988). A novel method for nucleic acid sequence determination. *Journal of Theoretical Biology*, 135(3):303-307.
Baskin, et al., "Copper-free click chemistry for dynamic in vivo imaging". PNAS, Oct. 23, 2007, vol. 104, No. 43, pp. 16793-16797.
Bentley et al. (2008). Accurate whole human genome sequencing using reversible terminator chemistry. *Nature*, 456:53-59.
Burgess et al. (1997). An Approach to Photolabile, Fluorescent Protecting Groups. *J. Org. Chem.*, 62:5165-5168.

(Continued)

*Primary Examiner* — Irina Krylova
(74) *Attorney, Agent, or Firm* — Knobbe, Martens, Olson & Bear, LLP

(57) ABSTRACT

Some embodiments described herein relate to a substrate with a surface comprising a silane or a silane derivative covalently attached to optionally substituted cycloalkene or optionally substituted heterocycloalkene for direct conjugation with a functionalized molecule of interest, such as a polymer, a hydrogel, an amino acid, a nucleoside, a nucleotide, a peptide, a polynucleotide, or a protein. In some embodiments, the silane or silane derivative contains optionally substituted norbornene or norbornene derivatives. Method for preparing a functionalized surface and the use in DNA sequencing and other diagnostic applications are also disclosed.

18 Claims, 16 Drawing Sheets

(56) References Cited

U.S. PATENT DOCUMENTS

| | | |
|---|---|---|
| 6,416,949 B1 | 7/2002 | Dower et al. |
| 6,465,178 B2 | 10/2002 | Chappa et al. |
| 6,482,591 B2 | 11/2002 | Lockhart et al. |
| 6,514,751 B2 | 2/2003 | Johann et al. |
| 6,524,793 B1 | 2/2003 | Chandler et al. |
| 6,610,482 B1 | 8/2003 | Fodor et al. |
| 6,890,741 B2 | 5/2005 | Fan et al. |
| 6,913,884 B2 | 7/2005 | Stuelpnagel et al. |
| 7,057,026 B2 | 6/2006 | Barnes et al. |
| 7,115,400 B1 | 10/2006 | Adessi et al. |
| 7,211,414 B2 | 5/2007 | Hardin et al. |
| 7,244,559 B2 | 7/2007 | Rothberg et al. |
| 7,315,019 B2 | 1/2008 | Turner et al. |
| 7,329,492 B2 | 2/2008 | Hardin et al. |
| 7,405,281 B2 | 7/2008 | Xu et al. |
| 7,582,420 B2 | 9/2009 | Oliphant et al. |
| 7,595,883 B1 | 9/2009 | El Gamal et al. |
| 7,622,294 B2 | 11/2009 | Walt et al. |
| 8,778,849 B2 | 7/2014 | Bowen et al. |
| 9,994,687 B2 | 6/2018 | Berti |
| 10,975,210 B2 | 4/2021 | Berti |
| 2002/0055100 A1 | 5/2002 | Kawashima et al. |
| 2002/0102578 A1 | 8/2002 | Dickinson et al. |
| 2004/0002090 A1 | 1/2004 | Mayer et al. |
| 2004/0096853 A1 | 5/2004 | Mayer et al. |
| 2005/0053980 A1 | 3/2005 | Gunderson et al. |
| 2005/0064460 A1 | 3/2005 | Holliger et al. |
| 2005/0130173 A1 | 6/2005 | Leamon et al. |
| 2005/0181440 A1 | 8/2005 | Chee et al. |
| 2005/0191698 A1 | 9/2005 | Chee et al. |
| 2006/0188901 A1 | 8/2006 | Barnes et al. |
| 2007/0003966 A1 | 1/2007 | Subhakar |
| 2007/0099208 A1 | 5/2007 | Drmanac et al. |
| 2007/0128624 A1 | 6/2007 | Gormley et al. |
| 2008/0009420 A1 | 1/2008 | Schroth et al. |
| 2008/0108082 A1 | 5/2008 | Rank et al. |
| 2009/0026082 A1 | 1/2009 | Rothberg et al. |
| 2009/0088327 A1 | 4/2009 | Rigatti |
| 2009/0117621 A1 | 5/2009 | Boutell |
| 2009/0118128 A1 | 5/2009 | Liu |
| 2009/0127589 A1 | 5/2009 | Rothberg et al. |
| 2009/0186349 A1 | 7/2009 | Gunderson et al. |
| 2009/0252774 A1 | 10/2009 | Masanao et al. |
| 2010/0111768 A1 | 5/2010 | Banerjee et al. |
| 2010/0137143 A1 | 6/2010 | Rothberg et al. |
| 2010/0282617 A1 | 11/2010 | Rothberg et al. |
| 2011/0009276 A1 | 1/2011 | Vermaas |
| 2011/0059865 A1 | 3/2011 | Smith et al. |
| 2011/0143966 A1 | 6/2011 | McGall et al. |
| 2011/0172118 A1 | 7/2011 | Kain et al. |
| 2011/0250353 A1 | 10/2011 | Caruso |
| 2012/0095203 A1 | 4/2012 | Bernardin et al. |
| 2012/0270305 A1 | 10/2012 | Reed et al. |
| 2012/0309634 A1 | 12/2012 | Rigatti |
| 2012/0316086 A1 | 12/2012 | Lin et al. |
| 2013/0116153 A1 | 5/2013 | Bowen et al. |
| 2013/0137861 A1 | 5/2013 | Leproust et al. |
| 2013/0165327 A1 | 6/2013 | Vermaas |
| 2013/0189287 A1 | 7/2013 | Bregeon |
| 2013/0338044 A1 | 12/2013 | Liao et al. |
| 2014/0079923 A1 | 3/2014 | George et al. |
| 2014/0243224 A1 | 8/2014 | Barnard et al. |
| 2016/0053252 A1 | 2/2016 | Von Hatten |

FOREIGN PATENT DOCUMENTS

| | | |
|---|---|---|
| EP | 2 532 639 A1 | 12/2012 |
| JP | 2004-085556 | 3/2004 |
| JP | 2009-255380 | 11/2009 |
| WO | WO 89/10977 A1 | 11/1989 |
| WO | WO 91/06678 A1 | 4/1991 |
| WO | WO 93/17126 A1 | 9/1993 |
| WO | WO 95/11995 A1 | 5/1995 |
| WO | WO 95/35505 A1 | 12/1995 |
| WO | WO 2000/031148 A2 | 6/2000 |
| WO | WO 2000/053812 A2 | 9/2000 |
| WO | WO 2000/063437 A2 | 10/2000 |
| WO | WO 2001/001143 A2 | 1/2001 |
| WO | WO 2001/062982 A2 | 8/2001 |
| WO | WO 2001/084234 A1 | 11/2001 |
| WO | WO 2002/012566 A2 | 2/2002 |
| WO | WO 2003/014392 A2 | 2/2003 |
| WO | WO 2004/018497 A2 | 3/2004 |
| WO | WO 2005/010145 A2 | 2/2005 |
| WO | WO 2007/123744 A2 | 11/2007 |
| WO | WO 2012/058096 A1 | 5/2012 |
| WO | WO 2013/036748 A1 | 3/2013 |
| WO | WO 2013/063382 A2 | 5/2013 |

OTHER PUBLICATIONS

Ciampi et al. (2010). Wet chemical routes to the assembly of organic monolayers on silicon surfaces via the formation of Si—C bonds; surface preparation, passivation and functionalization. *Chem. Soc. Rev.*, 39:2158-2183.

Dean et al. (2002). Comprehensive human genome amplification using multiple displacement amplification. *Proc Natl. Acad. Sci. USA*, 99(8):5261-5266.

Dressman et al. (2003). Transforming single DNA molecules into fluorescent magnetic particles for detection and enumeration of genetic variations. *Proc. Natl. Acad. Sci. USA*, 100(15):8817-8822.

Drmanac et al. (1998). Accurate sequencing by hybridization for DNA diagnostics and individual genomics. *Nature Biotechnology*, 16:54-58.

Efimov et al. (1999). Synthesis of polyacrylamides N-substituted with PNA-like oligonucleotide mimics for molecular diagnostic applications. *Nucleic Acids Research*, 27(22):4416-4426.

Fodor et al. (1991). Light-directed, spatially addressable parallel chemical synthesis. *Science*, 251(4995):767-773.

Gong, et al., "Simple Method to Prepare Oligonucleotide-Conjugated Antibodies and Its Application in Multiplex Protein Detection in Single Cells". Bioconjugate Chem. 2016, 27, 217-225.

Greene, T. W., & Wuts, P. G. M. (1999). *Protective Groups in Organic Synthesis*, 3rd Ed. New York: John Wiley & Sons, TOC, 10 pages.

Guillier et al. (2000). Linkers and cleavage strategies in solid-phase organic synthesis and combinatorial chemistry. *Chemical Reviews*, 100(6):2091-2158.

Gutsmiedl et al. (2009). Copper-free "click" modification of DNA via nitrile oxide-norbornene 1,3-dipolar cycloaddition. *Org. Lett.*, 11(11):2405-2408.

Hansell et al. (2011). Additive-free clicking for polymer functionalization and coupling by tetrazine-norbornene chemistr. *J. Am. Chem. Soc.*, 133:13828-13831.

Hermanson, G. T. (2013). *Bioconjugate Techniques*, 3rd Ed. New York: Academic Press, TOC, 4 pages.

Hoffmann, et al., "Universal protocol for grafting PCR primers onto various lab-on-a-chip substrates for solid-phase PCR". RSC Advances, 2012, 2, 3885-3889.

Hoyle et al. (2010). Thiol-click chemistry: a multifaceted toolbox for small molecule and polymer synthesis. *Chem. Soc. Rev.*, 39:1355-1387.

Huisgen et al. (1961). 1,3-Dipolar Cycloadditions. *Proc. Chem. Soc.*, pp. 357-369.

Jawalekar et al. (2011). Synthesis of isoxazoles by hypervalent iodine-induced cycloaddition of nitrile oxides to alkynes. *Chem. Commun.* 47:3198-3200.

Kaya et al. (2012). A Genetically Encoded Norbornene Amino Acid for the Mild and Selective Modification of Proteins in a Copper-Free Click Reaction. *Angew. Chem. Int. Ed.*, 51:4466-4469.

Kim et al. (2000). Surface-Initiated Ring-Opening Metathesis Polymerization on Si/SiO$_2$. *Macromolecules*, 33:2793-2795.

Korlach et al. (2008). Selective aluminum passivation for targeted immobilization of single DNA polymerase molecules in zero-mode waveguide nanostructures. *Proc. Natl. Acad. Sci. USA*, 105(4):1176-1181.

Lage et al. (2003). Whole genome analysis of genetic alterations in small DNA samples using hyperbranched strand displacement amplification and array-CGH. *Genome Research*, 13:294-307.

(56) References Cited

OTHER PUBLICATIONS

Lee et al. (1999). Studies on a Dithiane-Protected Benzoin Photolabile Safety Catch Linker for Solid-Phase Synthesis. *J. Org. Chem.*, 64:3454-3460.

Levene et al. (2003). Zero-mode waveguides for single-molecule analysis at high concentrations. *Science*, 299(5607):682-686.

Liu et al. (2005). Regioselective Ring-Opening/Cross-Metathesis Reactions of Norbornene Derivatives with Electron-Rich Olefins. *Org. Lett.*, 7(1):131-133.

Lizardi et al. (1998). Mutation detection and single-molecule counting using isothermal rolling-circle amplification. *Nature Genetics*, 19:225-232.

Lundquist et al. (2008). Parallel confocal detection of single molecules in real time. *Optics Letters*, 33(9):1026-1028.

McLay et al. (2010). Nitrones as dipoles for rapid strain-promoted 1,3-dipolar cycloadditions with cyclooctynes. *Chem. Commun.*, 46:931-933.

Mercier, et al., "Solid Phase DNA Amplification: A Brownian Dynamics Study of Crowding Effects". Biophysical Journal vol. 89 Jul. 2005 32-42.

Muller, et al., "Glossary of Terms Used in Physical Organic Chemistry", Pure & Appl. Chem., 1994, pp. 1077-1184.

Pedrow, et al., "Plasma-assisted Grafting of Polyethylene Glycol (PEG) to Solid Substrates". 2007 IEEE 34th International Conference on Plasma Science (ICOPS), Jun. 17-22, 2007, Albuquerque, NM. 1 page. DOI: 10.1109/PPPS.2007.4345870.

Perring, M. I. (2010). Functionalization and patterning of monolayers on silicon(111) and polydicyclopentadiene, PhD (Doctor of Philosophy thesis, University of Iowa http://ir.uiowa.edu/etd/722.

Ronaghi et al. (1996). Real-time DNA sequencing using detection of pyrophosphate release. *Analytical Biochemistry*, 242(1):84-89.

Ronaghi et al. (1998). A sequencing method based on real-time pyrophosphate. *Science*, 281(5375):363-365.

Ronaghi, M. (2001). Pyrosequencing sheds light on DNA sequencing. *Genome Research*, 11(1):3-11.

Sanders et al. (2011). Metal-Free Sequential [3+2]-Dipolar Cycloadditions using Cyclooctynes and 1,3-Dipoles of Different Reactivity. *J. Am. Chem. Soc.*, 133:949-957.

Scheiner et al. (1965). The Addition of Aryl Azides to Norbornene. A Kinetic Investigation. *J. Am. Chem. Soc.*, 87(2) 306-311.

Shea et al. (1992). Influence of Strain on Chemical Reactivity. Relative Reactivity of Torsionally Strained Double Bonds in 1,3-Dipolar Cycloadditions. *J. Am. Chem. Soc.*, 114:4846-4855.

Shendure et al. (2005). Accurate multiplex polony sequencing of an evolved bacterial genome. *Science*, 309:1728-1732.

Van Geel et al. (2012). Preventing Thiol-Yne Addition Improves the Specificity of Strain-Promoted Azide-Alkyne Cycloaddition. *Bioconjugate Chem.*, 23:392-398.

Walker et al. (1992). Strand displacement amplification—an isothermal, in vitro DNA amplification technique. *Nucleic Acids Research*, 20(7):1691-1696.

Walker et al. (1995). A chemiluminescent DNA probe test based on strand displacement amplification. In Danny L. Wiedbrauk and Daniel H. Farkas (Eds.), *Molecular Methods for Virus Detection* (pp. 329-349). San Diego: Academic Press, Inc.

Wolff, et al., "Über Diazoanhydride (1,2,3-Oxydiazole oder Diazoxyde) und Diazoketone", Justus Liebigs Ann. Chem., 394, 1912, 23-59.

Yao et al. (2012). Fluorophore Targeting to Cellular Proteins via Enzyme-Mediated Azide Ligation and Strain-Promoted Cycloaddition. *J. Am. Chem. Soc.*, 134:3720-3728.

Yingqiu et al. 2013. Gel immobilization of human genome. *Journal of Zhejiang University (Medical Sciences)*, 42(1):6-13.

Written Opinion of the International Preliminary Examining Authority mailed Jun. 26, 2015 for International Application No. PCT/US2014/044356 filed Jun. 26, 2014.

International Preliminary Report on Patentability mailed Oct. 9, 2015 for International Application No. PCT/US2014/044356 filed Jun. 26, 2014.

International Search Report and Written Opinion mailed Oct. 22, 2014 in International Application No. PCT/US2014/044356 filed Jun. 26, 2014.

| Lane | Tiles | Density (K/mm2) | Clusters PF (%) | Phas/Prephas (%) | Reads (M) | Reads PF (M) | % >= Q30 | Cycles Err Rated | Aligned (%) | Error Rate (%) | Intensity Cycle 1 | % Intensity Cycle 20 |
|---|---|---|---|---|---|---|---|---|---|---|---|---|
| 1 | 56 | 2164 +/- 0 | 59.5 +/- 6.8 | 0.134 / 0.252 | 176.81 | 105.22 | 86.4 | 25 | 96.8 +/- 1.1 | 0.26 +/- 0.05 | 3728 +/- 377 | 91.3 +/- 5.2 |
| 2 | 56 | 2164 +/- 0 | 61.1 +/- 5.7 | 0.130 / 0.248 | 176.81 | 108.07 | 87.2 | 25 | 97.2 +/- 0.8 | 0.25 +/- 0.05 | 3617 +/- 357 | 87.9 +/- 1.8 |
| 3 | 56 | 2164 +/- 0 | 61.1 +/- 6.4 | 0.135 / 0.298 | 176.81 | 108.03 | 87.7 | 25 | 97.3 +/- 0.9 | 0.24 +/- 0.05 | 3733 +/- 358 | 79.7 +/- 1.8 |
| 4 | 56 | 2164 +/- 0 | 61.2 +/- 6.3 | 0.133 / 0.310 | 176.81 | 108.2 | 87.5 | 25 | 97.4 +/- 1.0 | 0.25 +/- 0.06 | 3569 +/- 395 | 78.6 +/- 1.7 |
| 5 | 56 | 2164 +/- 0 | 60.1 +/- 5.4 | 0.118 / 0.295 | 176.81 | 106.27 | 87.3 | 25 | 97.3 +/- 0.8 | 0.24 +/- 0.05 | 3521 +/- 410 | 80.6 +/- 2.2 |
| 6 | 56 | 2164 +/- 0 | 58.9 +/- 12.8 | 0.123 / 0.286 | 176.81 | 104.11 | 87.9 | 25 | 94.0 +/- 18.4 | 0.25 +/- 0.06 | 3439 +/- 787 | 78.8 +/- 2.3 |
| 7 | 56 | 2164 +/- 0 | 60.2 +/- 6.2 | 0.117 / 0.307 | 176.81 | 106.37 | 87.4 | 25 | 97.2 +/- 1.1 | 0.25 +/- 0.06 | 3651 +/- 428 | 78.9 +/- 2.3 |
| 8 | 56 | 2164 +/- 0 | 58.8 +/- 7.2 | 0.119 / 0.356 | 176.81 | 104 | 86.5 | 25 | 96.6 +/- 1.5 | 0.27 +/- 0.07 | 3824 +/- 375 | 78.5 +/- 1.7 |

CATALYST-FREE SURFACE FUNCTIONALIZATION AND POLYMER GRAFTING

CROSS-REFERENCE TO RELATED APPLICATIONS

The present application is a divisional of U.S. application Ser. No. 17/194,019, filed Mar. 5, 2021, to be issued as U.S. Pat. No. 11,618,808, which is a continuation of U.S. application Ser. No. 15/989,079, filed May 24, 2018, now U.S. Pat. No. 10,975,210, which is a continuation of U.S. application Ser. No. 14/316,478, filed Jun. 26, 2014, now U.S. Pat. No. 9,994,687, which claims the benefit of priority to U.S. Provisional Patent Application No. 61/841,647 filed on Jul. 1, 2013, and U.S. Provisional Patent Application No. 61/971,381 filed on Mar. 27, 2014, all of which are hereby expressly incorporated by reference in their entireties.

FIELD

In general, the present application relates to the fields of chemistry, biology and material science. More specifically, the present application relates to a substrate with a surface comprising a silane or silane derivative comprising optionally substituted unsaturated moieties comprising cycloalkenes, cycloalkynes, heterocycloalkenes, or heterocycloalkynes covalently attached thereto for direct conjugation with a functionalized molecule of interest. Methods for preparing a functionalized surface and the use in DNA sequencing and other diagnostic applications are also disclosed.

BACKGROUND

Polymer or hydrogel-coated substrates are used in many technological applications. For example, implantable medical devices can be coated with biologically inert polymers. In another example, polymer or hydrogel coated substrates are used for the preparation and/or analysis of biological molecules. Molecular analyses, such as certain nucleic acid sequencing methods, rely on the attachment of nucleic acid strands to a polymer or hydrogel-coated surface of a substrate. The sequences of the attached nucleic acid strands can then be determined by a number of different methods that are well known in the art.

In certain sequencing-by-synthesis processes, one or more surfaces of a flow cell are coated with a polymer or a hydrogel to which nucleic acids are attached. Current commercial flow cells utilize a non-attached gel coating. Use of an appropriate conjugating chemistry may provide for commercially viable flow cells having covalently attached gel coatings. Considerations such as cost of materials, compatibility with manufacturing processes, stability during storage and shipping, and the ability to support downstream chemical processing steps such as nucleic acid amplification and sequencing are important to consider. This disclosure provides a particularly useful chemistry having several advantages as will become apparent from the disclosure.

SUMMARY

The present application discloses new ways to prepare the surface of a substrate for direct conjugation of an appropriately functionalized hydrogel, polymer, molecule or biomolecule of interest. The surface is treated with a silane or a silane derivative comprising a first plurality of optionally substituted unsaturated moieties selected from cycloalkenes, cycloalkynes, heterocycloalkenes, or heterocycloalkynes covalently bounded to the silicon atoms of the silane or silane derivative either directly or via linkers, such as norbornene, cyclooctene, cyclooctyne, bicycloalkynes, or any cycloalkenes, cycloalkynes, heterocycloalkenes, heterocycloalkynes or derivatives thereof where ring strain is present, without the need of catalyst or additional cross-linking agents. In particular embodiments, the implementation of the present application eliminates the use of additional cross-linking compounds or catalysts, and provides a single surface modification process as a common starting point to obtain a large variety of functionalized surfaces for use in DNA sequencing and other diagnostic applications. In addition, substrate surfaces prepared accordingly to the present application were found to have higher stability resulting in longer shelf life and reduced surface contamination upon storage. Lastly, substrate surfaces prepared according to the present application were found to have unique surface affinity compared to standard silanes (such as APTES or APTMS), which resulted in better wettability with aqueous based components and more homogeneous coatings.

The present application also discloses new ways to graft primers to the surface of a substrate. In one embodiment, the surface is treated with silane or a silane derivative comprising a first plurality of optionally substituted unsaturated moieties selected from cycloalkenes, cycloalkynes, heterocycloalkenes, or heterocycloalkynes covalently bounded to the silicon atoms of the silane or silane derivative either directly or via linkers, without the need of catalyst or additional cross-linking agents. Then, the primer is pre-conjugated with a functional molecule with functional groups covalently bonded to oligonucleotides, where the oligonucleotides comprises a second plurality of optionally substituted unsaturated moieties selected from cycloalkenes, cycloalkynes, heterocycloalkenes, or heterocycloalkynes, such as cyclooctyne or bicycloalkynes, e.g., bicyclo[6.1.0]non-4-yne. Finally, the pre-conjugated primer is covalently attached to the silane or silane derivative by reacting the functional groups of the functionalized molecule with the unsaturated moieties of the silane or silane derivative.

Some embodiments described herein relate to a substrate comprising a first surface comprising silane or a silane derivative covalently bound to a functionalized molecule through a first plurality of unsaturated moieties selected from cycloalkenes, cycloalkynes, heterocycloalkenes, heterocycloalkynes, or optionally substituted variants or combinations thereof covalently attached to silicon atoms of the silane or silane derivative. In some embodiments, the substrate further comprises oligonucleotides covalently attached to the functionalized molecule through a second plurality of unsaturated moieties selected from cycloalkenes, cycloalkynes, heterocycloalkenes, heterocycloalkynes, or optionally substituted variants or combinations thereof.

Some embodiments described herein relate to a method of immobilizing a functionalized molecule comprising functional groups to a first surface of a substrate, the method comprising: applying silane or a silane derivative comprising a first plurality of unsaturated moieties selected from cycloalkenes, cycloalkynes, heterocycloalkenes, heterocycloalkynes, or optionally substituted variants or combinations thereof covalently attached thereto onto the first surface of the substrate; and covalently attaching the functionalized molecule to the silane or silane derivative by reacting the functional groups of the functionalized molecule with the first plurality of unsaturated moieties to form a coating layer. In some embodiments, the method further comprises providing oligonucleotides comprising a second plurality of unsaturated moieties selected from cycloalkenes, cycloalkynes, heterocycloalkenes, heterocycloalkynes, or optionally substituted variants or combinations thereof; and reacting the second plurality of unsaturated moieties of the oligonucleotides with the functional groups of the functionalized molecule to form covalent bonding.

Some embodiments described herein relate to a method of grafting primers to a first surface of a substrate, the method comprising:
providing a substrate comprising a coating layer on a first surface of the substrate, wherein the coating layer comprises silane or a silane derivative covalently bound to a functionalized molecule comprising functional groups through a first plurality of unsaturated moieties of the silane or silane derivative, and wherein the first plurality of unsaturated moieties are selected from cycloalkenes, cycloalkynes, heterocycloalkenes, heterocycloalkynes, or optionally substituted variants or combinations thereof;
contacting oligonucleotides comprising a second plurality of unsaturated moieties selected from cycloalkenes, cycloalkynes, heterocycloalkenes, heterocycloalkynes, or optionally substituted variants or combinations thereof with the coating layer; and
reacting the second plurality of unsaturated moieties of the oligonucleotides with the functional groups of the functionalized molecule to form covalent bonding. In some embodiments, the coating layer is prepared by applying silane or a silane derivative comprising the first plurality of unsaturated moieties onto the first surface of the substrate, and covalently attaching the functionalized molecule to the silane or silane derivative by reacting the functional groups of the functionalized molecule with the first plurality of unsaturated moieties.

Some embodiments described herein relate to a method of grafting primers on a first surface of a substrate, the method comprising:
providing a substrate having a first surface comprising silane or a silane derivative, wherein said silane or silane derivative comprises a first plurality of unsaturated moieties selected from cycloalkenes, cycloalkynes, heterocycloalkenes, heterocycloalkynes, or optionally substituted variants or combinations thereof covalently attached thereto onto the first surface of the substrate;
providing pre-conjugated primers comprising oligonucleotides covalently attached to a functionalized molecule, wherein said functionalized molecule comprises functional groups; and
contacting the pre-conjugated primers with the silane or silane derivative such that the pre-conjugated primers are covalently attached to the first surface of the substrate by reacting the functional groups of the functionalized molecule with the first plurality of unsaturated moieties of the silane or silane derivative to form covalent bonding.

In some embodiments, the first surface of the substrate is pre-treated with silane or a silane derivative described herein. In some embodiments, the pre-conjugated primers are prepared by reacting a second plurality of unsaturated moieties of the oligonucleotides with the functional groups of the functionalized molecule to form covalent bonds, wherein the second plurality of unsaturated moieties are selected from cycloalkenes, cycloalkynes, heterocycloalkenes, heterocycloalkynes, or optionally substituted variants or combinations thereof.

In any of the embodiments described herein, the first plurality of unsaturated moieties can be selected from norbornene, heteronorbornenes, norbornene derivatives, trans-cyclooctene, trans-cyclooctene derivatives, cyclooctyne, bicycloalkynes, or optionally substituted variants or combinations thereof. In some other embodiments, any other cycloalkenes, cycloalkynes, heterocycloalkenes, or heterocycloalkynes presenting ring strain can also be used. In some embodiments, the first plurality of unsaturated moieties can be optionally substituted norbornenes. In some embodiments, the first plurality of unsaturated moieties can be optionally substituted cyclooctyne. In some embodiment, the first plurality of unsaturated moieties can be selected from optionally substituted bicyclononynes. In some embodiments, the optionally substituted bicyclononynes comprise bicyclo[6.1.0]non-4-yne.

In any of the embodiments described herein, the second plurality of unsaturated moieties of the oligonucleotides can be selected from norbornene, heteronorbornenes, norbornene derivatives, trans-cyclooctene, trans-cyclooctene derivatives, cyclooctyne, bicycloalkynes, or optionally substituted variants or combinations thereof. In some other embodiments, any other cycloalkenes, cycloalkynes, heterocycloalkenes, or heterocycloalkynes presenting ring strain can also be used. In some embodiments, the second plurality of unsaturated moieties can be optionally substituted cyclooctyne. In some embodiments, the second plurality of unsaturated moieties can be optionally substituted bicyclononynes. In some further embodiments, the optionally substituted bicyclononynes comprise bicyclo[6.1.0]non-4-yne.

In any of the embodiments described herein, the silane or silane derivative can comprise the following formula:

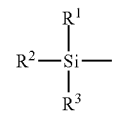

where $R^1$, $R^2$ and $R^3$ can each be independently selected from hydrogen, halogen, optionally substituted alkyl, optionally substituted alkoxy, optionally substituted aryl, optionally substituted aryloxy, optionally substituted heteroaryl or optionally substituted heteroaryloxy. In some embodiments, each $R^1$, $R^2$ and $R^3$ can be independently selected from optionally substituted alkoxy. In some such embodiments, each of $R^1$, $R^2$ and $R^3$ is methoxy.

In any of the embodiments described herein, the silane or silane derivative can be applied onto the first surface by chemical vapor deposition. In some other embodiments, the silane or silane derivative can be applied onto the first surface by Yield Engineering Systems (YES) method.

In any of the embodiments described herein, the silane or silane derivative further comprises linkers covalently attached between silicon atoms of the silane or silane derivative and the first plurality of unsaturated moieties. In some such embodiments, the linkers are selected from optionally substituted alkylenes, optionally substituted heteroalkylenes, optionally substituted cycloalkylenes, optionally substituted heterocyclylenes, optionally substituted arylenes, optionally substituted heteroarylenes, optionally substituted polyethylene glycols, cleavable linkers, or combinations thereof. In some such embodiments, the linkers are optionally substituted alkylene linkers. In some further such embodiments, the linkers are optionally substituted ethylene linker. In some other such embodiments, the linkers are cleavable linkers. In some such embodiments, the cleavable linkers are selected from (—S—S—), esters, nitrobenzene, imines, peptides, oligonucleotides, or polynucleotides.

In any of the embodiments described herein, the functionalized molecule comprises a polymer, a hydrogel, an amino acid, a peptide, a nucleoside, a nucleotide, a polynucleotide, a protein, or combinations thereof. In some embodiments, the functionalized molecule is selected from a polymer, a hydrogel, an amino acid, a peptide, a nucleoside, a nucleotide, a polynucleotide, a protein, or combinations thereof. In some further embodiments, the functionalized molecule is a hydrogel or a polymer comprising one or more functional groups selected from azido, optionally substituted amino, optionally substituted alkenyl, optionally substituted hydrazone, optionally substituted hydrazine, carboxyl, hydroxy, optionally substituted tetrazole, optionally substituted tetrazine, nitrile oxide, nitrone or thiol. In some embodiments, the functionalized molecule comprises a polymer or hydrogel comprising a recurring unit of Formula (I) and a recurring unit of formula (II) as described below in the Detailed Description of Embodiments. In some embodiments, the functionalized molecule comprises a polymer comprising Formula (III) or (III') as described below in the Detailed Description of Embodiments.

In any of the embodiments described herein, the functionalized molecule comprises functional groups selected from optionally substituted alkenyl, azido, optionally substituted amino, carboxyl, optionally substituted hydrazone, optionally substituted hydrazine, hydroxy, optionally substituted tetrazole, optionally substituted tetrazine, nitrile oxide, nitrone, or thiol, provided that the functionalized molecule is not norbornene or polymerized norbornene. In some such embodiments, the functionalized molecule comprises azido groups. In some embodiments, the functionalized molecule is poly(N-(5-azidoacetamidylpentyl)acrylamide-co-acrylamide) (PAZAM).

In any of the embodiments described herein, the substrate is selected from glass substrate, silica substrate, quartz, plastic substrate, metal substrate, metal oxide substrate, or combinations thereof. In one embodiment, the substrate is a glass substrate.

In any of the embodiments described herein, the first surface comprises both functionalized molecules coated regions and inert regions. In some embodiments, the inert regions are selected from glass regions, metal regions, mask regions and interstitial regions, or combinations thereof. In one embodiment, the inert regions comprise glass.

In any of the embodiments of the methods described herein, the method can further comprise a washing step to remove excess unbounded functionalized molecules.

In any of the embodiments of the methods described herein, the method can further comprise a drying step.

In any of the embodiments of the methods for grafting primers as described herein, the method can further comprise a washing step to remove excess unbounded oligonucleotides.

BRIEF DESCRIPTION OF THE DRAWINGS

FIG. 4 shows the sequencing metrics of the grafted primer from the substrate prepared by the procedure described in Example 1.

DETAILED DESCRIPTION OF EMBODIMENTS

Figure 1A:
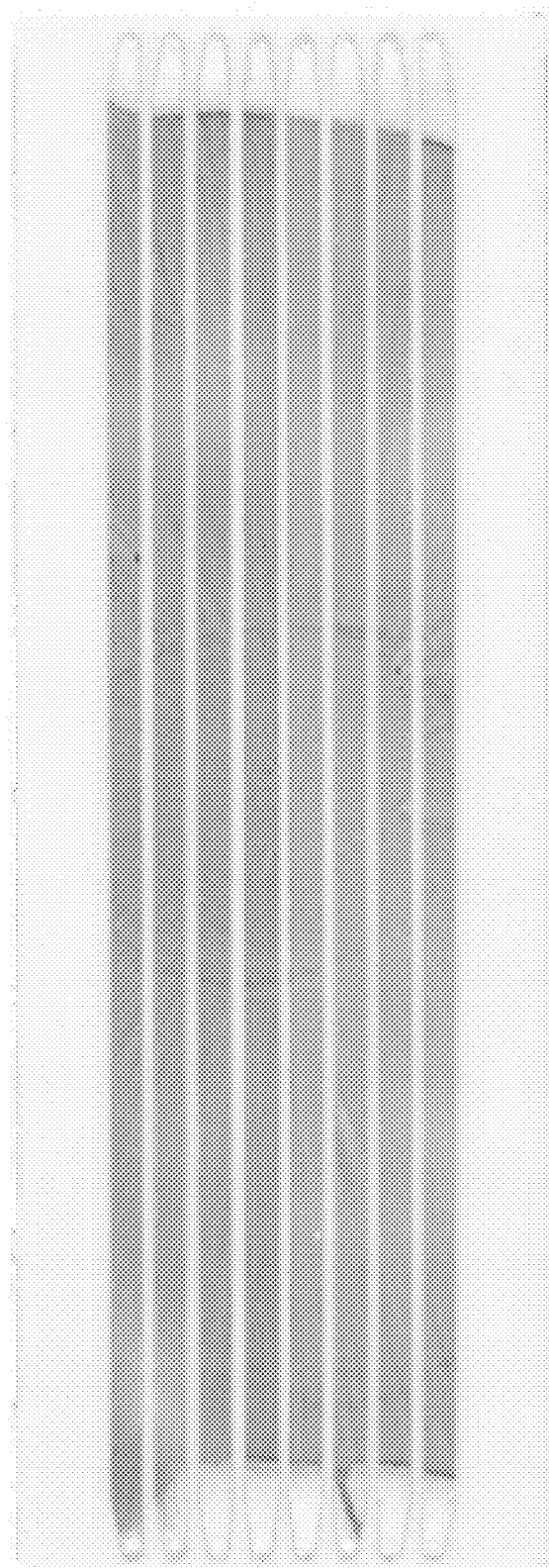
FIG. 1A shows a glass substrate silanized with a norbornene-silane derivative [(5-bicyclo[2.2.1]hept-2-enyl) ethyl]trimethoxysilane (1a) and subsequently coated and thermally cross-linked with PAZAM.

Embodiments of the invention relate to the conjugation of a functionalized molecule to the surface of a substrate functionalized with silane or a silane derivative having optionally substituted unsaturated moieties selected from cycloalkenes, cycloalkynes, heterocycloalkenes, or heterocycloalkynes covalently bonded to the silicon atoms of the silane or silane derivative. In one embodiment, the functionalized molecule is a hydrogel, polymer or other molecule that is desired to be attached to a substrate. In some embodiments, the functionalized molecule is conjugated to a surface through a norbornene derivative, such as a norbornene-derivatized silane, such as [(5-bicyclo[2.2.1]hept-2-enyl)ethyl]trimethoxysilane. In some embodiments, the functionalized molecule is conjugated to a surface through a cycloalkyne-derivatized silane, such as cyclooctyne or a bicyclononyne-derivatized silane, for example, bicyclo[6.1.0]non-4-yne derivatized silane, or mixtures thereof.

Some embodiments relate to a flow cell for performing sequencing-by-synthesis reactions that includes a hydrogel, such as poly(N-(5-azidoacetamidylpentyl) acrylamide-co-acrylamide) ("PAZAM") conjugated to a glass substrate through a norbornene-derivatized silane linkage, a cyclooctyne-derivatized silane linkage, or a bicyclononyne-derivatized silane linkage.

Some embodiments related to a flow cell for performing sequencing-by-synthesis reactions that include oligonucleotides, such as a P5 or P7 primer conjugated to a hydrogel or polymer coated substrate surface through cyclooctyne or bicyclononyne-derivatized linkage, such as bicyclo[6.1.0]non-4-yne derivatized linkage.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

The section headings used herein are for organizational purposes only and are not to be construed as limiting the subject matter described.

As used herein, common organic abbreviations are defined as follows:
Ac Acetyl
$Ac_2O$ Acetic anhydride
APTS aminopropyl silane
APTES (3-aminopropyl)triethoxy silane
APTMS (3-aminopropyl)trimethoxysilane
aq. Aqueous
Azapa N-(5-azidoacetamidylpentyl) acrylamide
BCN Bicyclo[6.1.0]non-4-yne
BHT Butylated hydroxyl toluene
Bn Benzyl
Brapa or BRAPA N-(5-bromoacetamidylpentyl) acrylamide
Bz Benzoyl
BOC or Boc tert-Butoxycarbonyl
Bu n-Butyl
cat. Catalytic
Cbz Carbobenzyloxy
CMP Chemical mechanical polishing
CyCl Cyanuric chloride
CVD Chemical vapor deposition
° C. Temperature in degrees Centigrade
dATP Deoxyadenosine triphosphate
dCTP Deoxycytidine triphosphate
dGTP Deoxyguanosine triphosphate
dTTP Deoxythymidine triphosphate
DBU 1,8-Diazabicyclo[5.4.0]undec-7-ene
DCA Dichloroacetic acid
DCE 1,2-Dichloroethane
DCM Methylene chloride
DIPEA Diisopropylethylamine
DMA Dimethylacetamide
DME Dimethoxyethane
DMF N,N'-Dimethylformamide
DMSO Dimethylsulfoxide
DPPA Diphenylphosphoryl azide
Et Ethyl
EtOAc Ethyl acetate
g Gram(s)
GPC Gel permeation chromatography
h or hr Hour(s)
iPr Isopropyl
KPi 10 mM potassium phosphate buffer at pH 7.0
KPS Potassium persulfate
IPA Isopropyl Alcohol
LCMS Liquid chromatography-mass spectrometry
LDA Lithium diisopropylamide
m or min Minute(s)
mCPB A meta-Chloroperoxybenzoic Acid
MeOH Methanol
MeCN Acetonitrile
mL Milliliter(s)
MTBE Methyl tertiary-butyl ether
$NaN_3$ Sodium Azide
NHS N-hydroxysuccinimide
NHS-AA Acrylic acid N-hydroxysuccinimide ester
PAZAM poly(N-(5-azidoacetamidylpentyl) acrylamide-co-acrylamide) of any acrylamide to Azapa ratio
PG Protecting group
Ph Phenyl
PMDETA N,N,N',N",N"-Pentamethyldiethylenetriamine
ppt Precipitate
rt Room temperature
SBS Sequencing-by-Synthesis
SFA Silane Free Acrylamide as defined in U.S. Pat. Pub. No. 2011/0059865
Sulfo-HSAB or SHSAB N-Hydroxysulfosuccinimidyl-4-azidobenoate
TEA Triethylamine
TEMPO (2,2,6,6-Tetramethylpiperidin-1-yl)oxyl
TCDI 1,1'-Thiocarbonyl diimidazole
Tert, t tertiary
TFA Trifluoroacetic acid
THF Tetrahydrofuran TEMED Tetramethylethylenediamine
YES Yield Engineering Systems
μL Microliter(s)

As used herein, the term "array" refers to a population of different probe molecules that are attached to one or more substrates such that the different probe molecules can be differentiated from each other according to relative location. An array can include different probe molecules that are each located at a different addressable location on a substrate. Alternatively or additionally, an array can include separate substrates each bearing a different probe molecule, wherein the different probe molecules can be identified according to the locations of the substrates on a surface to which the substrates are attached or according to the locations of the substrates in a liquid. Exemplary arrays in which separate substrates are located on a surface include, without limitation, those including beads in wells as described, for example, in U.S. Pat. No. 6,355,431 B1, US 2002/0102578 and PCT Publication No. WO 00/63437. Exemplary formats that can be used in the present application to distinguish beads in a liquid array, for example, using a microfluidic device, such as a fluorescent activated cell sorter (FACS), are described, for example, in U.S. Pat. No. 6,524,793. Further examples of arrays that can be used in the application include, without limitation, those described in U.S. Pat. Nos. 5,429,807; 5,436,327; 5,561,071; 5,583,211; 5,658,734; 5,837,858; 5,874,219; 5,919,523; 6,136,269; 6,287,768; 6,287,776; 6,288,220; 6,297,006; 6,291,193; 6,346,413; 6,416,949; 6,482,591; 6,514,751 and 6,610,482; and WO 93/17126; WO 95/11995; WO 95/35505; EP 742 287; and EP 799 897.

As used herein, the term "covalently attached" or "covalently bonded" refers to the forming of a chemical bonding that is characterized by the sharing of pairs of electrons between atoms. For example, a covalently attached polymer coating refers to a polymer coating that forms chemical bonds with a functionalized surface of a substrate, as compared to attachment to the surface via other means, for example, adhesion or electrostatic interaction. It will be appreciated that polymers that are attached covalently to a surface can also be bonded via means in addition to covalent attachment, for example, physisorption.

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkylthio" refers to the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atoms, although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. The heteroalkyl group may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain.

As used herein, "alkylene" means a branched, or straight chain fully saturated di-radical chemical group containing only carbon and hydrogen that is attached to the rest of the molecule via two points of attachment (i.e., an alkanediyl). The alkylene group may have 1 to 20,000 carbon atoms, although the present definition also covers the occurrence of the term alkylene where no numerical range is designated. The alkylene group may also be a medium size alkylene having 1 to 9 carbon atoms. The alkylene group could also be a lower alkylene having 1 to 4 carbon atoms. The alkylene group may be designated as "$C_{1-4}$ alkylene" or similar designations. By way of example only, "$C_{1-4}$ alkylene" indicates that there are one to four carbon atoms in the alkylene chain, i.e., the alkylene chain is selected from the group consisting of methylene, ethylene, ethan-1,1-diyl, propylene, propan-1,1-diyl, propan-2,2-diyl, 1-methyl-ethylene, butylene, butan-1,1-diyl, butan-2,2-diyl, 2-methyl-propan-1,1-diyl, 1-methyl-propylene, 2-methyl-propylene, 1,1-dimethyl-ethylene, 1,2-dimethyl-ethylene, and 1-ethyl-ethylene.

As used herein, the term "heteroalkylene" refers to an alkylene chain in which one or more skeletal atoms of the alkylene are selected from an atom other than carbon, e.g., oxygen, nitrogen, sulfur, phosphorus or combinations thereof. The heteroalkylene chain can have a length of 2 to 20,000. Exemplary heteroalkylenes include, but are not limited to, —OCH$_2$—, —OCH(CH$_3$)—, —OC(CH$_3$)$_2$—, —OCH$_2$CH$_2$—, —CH(CH$_3$)O—, —CH$_2$OCH$_2$—, —CH$_2$OCH$_2$CH$_2$—, —SCH$_2$—, —SCH(CH$_3$)—, —SC(CH$_3$)$_2$—, —SCH$_2$CH$_2$—, —CH$_2$SCH$_2$CH$_2$—, —NHCH$_2$—, —NHCH(CH$_3$)—, —NHC(CH$_3$)$_2$—, —NHCH$_2$CH$_2$—, —CH$_2$NHCH$_2$—, —CH$_2$NHCH$_2$CH$_2$—, and the like.

As used herein, "alkenylene" means a straight or branched chain di-radical chemical group containing only carbon and hydrogen and containing at least one carbon-carbon double bond that is attached to the rest of the molecule via two points of attachment. The alkenylene group may have 2 to 20,000 carbon atoms, although the present definition also covers the occurrence of the term alkenylene where no numerical range is designated. The alkenylene group may also be a medium size alkenylene having 2 to 9 carbon atoms. The alkenylene group could also be a lower alkenylene having 2 to 4 carbon atoms. The alkenylene group may be designated as "$C_{2-4}$ alkenylene" or similar designations. By way of example only, "$C_{2-4}$ alkenylene" indicates that there are two to four carbon atoms in the alkenylene chain, i.e., the alkenylene chain is selected from the group consisting of ethenylene, ethen-1,1-diyl, propenylene, propen-1,1-diyl, prop-2-en-1,1-diyl, 1-methyl-ethenylene, but-1-enylene, but-2-enylene, but-1,3-dienylene, buten-1,1-diyl, but-1,3-dien-1,1-diyl, but-2-en-1,1-diyl, but-3-en-1,1-diyl, 1-methyl-prop-2-en-1,1-diyl, 2-methyl-prop-2-en-1,1-diyl, 1-ethyl-ethenylene, 1,2-dimethyl-ethenylene, 1-methyl-propenylene, 2-methyl-propenylene, 3-methyl-propenylene, 2-methyl-propen-1,1-diyl, and 2,2-dimethyl-ethen-1,1-diyl.

As used herein, "alkynylene" means a straight or branched chain di-radical chemical group containing only carbon and hydrogen and containing at least one carbon-carbon triple bond that is attached to the rest of the molecule via two points of attachment.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "arylene" refers to an aromatic ring or ring system containing only carbon and hydrogen that is attached to the rest of the molecule via two points of attachment.

As used herein, "aryloxy" and "arylthio" refers to RO— and RS—, in which R is an aryl as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinolinyl, benzimidazolyl, benzoxazolyl, benzothiazolyl, indolyl, isoindolyl, and benzothienyl.

As used herein, "heteroarylene" refers to an aromatic ring or ring system containing one or more heteroatoms in the ring backbone that is attached to the rest of the molecule via two points of attachment.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazolylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "cycloalkylene" means a fully saturated carbocyclyl ring or ring system that is attached to the rest of the molecule via two points of attachment.

As used herein, "cycloalkenyl" or "cycloalkene" means a carbocyclyl ring or ring system having at least one double bond, wherein no ring in the ring system is aromatic. An example is cyclohexenyl or cyclohexene. Another example is norbornene or norbornenyl.

As used herein, "heterocycloalkenyl" or "heterocycloalkene" means a carbocyclyl ring or ring system with at least one heteroatom in ring backbone, having at least one double bond, wherein no ring in the ring system is aromatic.

As used herein, "cycloalkynyl" or "cycloalkyne" means a carbocyclyl ring or ring system having at least one triple bond, wherein no ring in the ring system is aromatic. An example is cyclooctyne. Another example is bicyclononyne.

As used herein, "heterocycloalkynyl" or "heterocycloalkyne" means a carbocyclyl ring or ring system with at least one heteroatom in ring backbone, having at least one triple bond, wherein no ring in the ring system is aromatic.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidinyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

As used herein, "heterocyclylene" means a non-aromatic cyclic ring or ring system containing at least one heteroatom that is attached to the rest of the molecule via two points of attachment.

A "(heterocyclyl)alkyl" is a heterocyclyl group connected, as a substituent, via an alkylene group. Examples include, but are not limited to, imidazolinylmethyl and indolinylethyl.

As used herein, "acyl" refers to —C(═O)R, wherein R is hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. Non-limiting examples include formyl, acetyl, propanoyl, benzoyl, and acryl.

An "O-carboxy" group refers to a "—OC(═O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-carboxy" group refers to a "—C(═O)OR" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes carboxyl (i.e., —C(═O)OH).

An "acetal" group refers to RC(H)(OR')$_2$, in which R and R' are independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(═O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "sulfonyl" group refers to an "—SO$_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "S-sulfonamido" group refers to a "—SO$_2$NR$_A$R$_B$" group in which R$_A$ and R$^B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-sulfonamido" group refers to a "—N(R$_A$)SO$_2$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "nitrile oxide" as used herein, refers to a "RC≡N⁺O⁻" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, or 5-10 membered heterocyclyl, as defined herein. Non-limiting examples of preparing nitrile oxide include in situ generation from aldoximes by treatment with chloramide-T or through action of base on imidoyl chlorides [RC(Cl)=NOH].

An "nitrone" as used herein, refers to a "$R_A R_B C=NR_C^+ O^-$" group in which $R_A$, $R_B$ and $R_C$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, or 5-10 membered heterocyclyl, as defined herein.

An "O-carbamyl" group refers to a "—OC(=O)$NR_A R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-carbamyl" group refers to an "—N($R_A$)OC(=O)$R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-thiocarbamyl" group refers to a "—OC(=S)$NR_A R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-thiocarbamyl" group refers to an "—N($R_A$)OC(=S)$R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-amido" group refers to a "—C(=O)$NR_A R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-amido" group refers to a "—N($R_A$)C(=O)$R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "amino" group refers to a "—$NR_A R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes free amino (i.e., —$NH_2$).

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

The term "hydrazine" or "hydrazinyl" as used herein refers to a —$NHNH_2$ group.

The term "hydrazone" or "hydrazonyl" as used herein refers to a

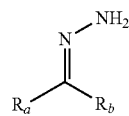

group.

The term "formyl" as used herein refers to a —C(O)H group.

The term "epoxy" as used herein refers to

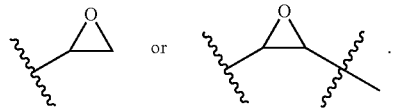

The term "ester" as used herein refers to R—C(=O)O—R', wherein R and R' can be independently alkyl, alkenyl, alkynyl, cycloalkyl, cycloalkenyl, cycloalkynyl, aryl, heteroaryl, heteroalicyclyl, aralkyl, (heteroalicyclyl)alkyl, or optionally substituted variants thereof.

The term "carboxylic acid" or "carboxyl" as used herein refers to —C(O)OH.

The term "thiocyanate" as used herein refers to —S—C≡N group.

The term "oxo-amine" as used herein refers to —O—$NH_2$ group, wherein one or more hydrogen of the —$NH_2$ can be optionally substituted by a R group. R can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl.

As used herein, a "nucleotide" includes a nitrogen containing heterocyclic base, a sugar, and one or more phosphate groups. They are monomeric units of a nucleic acid sequence. In RNA, the sugar is a ribose, and in DNA a deoxyribose, i.e. a sugar lacking a hydroxyl group that is present at the 2' position in ribose. The nitrogen containing heterocyclic base can be purine or pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine.

As used herein, a "nucleoside" is structurally similar to a nucleotide, but lacks any phosphate moieties at the 5' position. The term "nucleoside" is used herein in its ordinary sense as understood by those skilled in the art. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers.

As used herein, the term "polynucleotide" refers to nucleic acids in general, including DNA (e.g. genomic DNA cDNA), RNA (e.g. mRNA), synthetic oligonucleotides and synthetic nucleic acid analogs. Polynucleotides may include natural or non-natural bases, or combinations thereof and natural or non-natural backbone linkages, e.g. phosphorothioates, PNA or 2'-O-methyl-RNA, or combinations thereof.

As used herein, a "BCN primer" or "BCN modified primer" refers to a primer comprising covalently attached bicyclo[6.1.0]non-4-yne at the 5' terminus. The primer is defind as a single strand DNA (ssDNA) molecule with a free 3' OH group and a modification at the 5' terminus to allow the coupling reactions. The primer length can be any number of bases long and can include a variety of non natural nucleotides.

As used herein, the term "silane" refers to an organic or inorganic compound containing one or more silicon atoms. Non-limiting example of an inorganic silane compound is $SiH_4$, or halogenated $SiH_4$ where hydrogen is replaced by one or more halogen atoms. Non-limiting example of an organic silane compound is $X—R^C—Si(OR^D)_3$, wherein X is a non-hydrolyzable organic group, such as amino, vinyl, epoxy, methacrylate, sulfur, alkyl, alkenyl, alkynyl; $R^C$ is a spacer, for example $—(CH_2)_n—$, wherein n is 0 to 1000; $R^D$ is selected from hydrogen, optionally substituted alkyl, optionally substituted alkenyl, optionally substituted alkynyl, optionally substituted carbocyclyl, optionally substituted aryl, optionally substituted 5-10 membered heteroaryl, and optionally substituted 5-10 membered heterocyclyl, as defined herein. As used herein, the term "silane" can comprise mixtures of different silane compounds.

As used herein, the term "tetrazine" or "tetrazinyl" refers to six-membered heteroaryl group comprising four nitrogen atoms. Tetrazine can be optionally substituted.

As used herein, the term "tetrazole" or "tetrazolyl" refers to five membered heterocyclic group comprising four nitrogen atoms. Tetrazole can be optionally substituted.

As used herein, the term "unsaturated moiety" refers to a chemical group includes cycloalkenes, cycloalkynes, heterocycloalkenes, heterocycloalkynes, or optionally substituted variants thereof comprising at least one double bond or one triple bond. The unsaturated moieties can be mono-valent or di-valent. When the unsaturated moiety is mono-valent, cycloalkene, cycloalkyne, heterocycloalkene, heterocycloalkyne are used interchangeably with cycloalkenyls, cycloalkynyls, heterocycloalkenyl, heterocycloalkynyl. When the unsaturated moiety is di-valent, cycloalkene, cycloalkyne, heterocycloalkene, heterocycloalkyne are used interchangeably with cycloalkenylene, cycloalkynylene, heterocycloalkenylene, heterocycloalkynylene.

As used herein, the term "polymer" refers to a molecule composed of many repeated subunits. Polymers can be linear, branched, or hyperbranched. Non-limiting examples of branched polymers include star polymers, comb polymers, brush polymers, dendronized polymers, ladders, and dendrimers. The polymers described herein can also be in the form of polymer nanoparticles.

As used herein, the prefixes "photo" or "photo-" mean relating to light or electromagnetic radiation. The term can encompass all or part of the electromagnetic spectrum including, but not limited to, one or more of the ranges commonly known as the radio, microwave, infrared, visible, ultraviolet, X-ray or gamma ray parts of the spectrum. The part of the spectrum can be one that is blocked by a metal region of a surface such as those metals set forth herein. Alternatively or additionally, the part of the spectrum can be one that passes through an interstitial region of a surface such as a region made of glass, plastic, silica, or other material set forth herein. In particular embodiments, radiation can be used that is capable of passing through a metal. Alternatively or additionally, radiation can be used that is masked by glass, plastic, silica, or other material set forth herein.

As used herein, the term "reactive site" means a site on the functionalized molecule coatings described herein that can be used to attach one or more molecules by way of a chemical reaction or molecular interaction. Such attachment may be via a covalent bond or through other bonding or interactive forces.

As used herein, the term "YES method" refers to the chemical vapor deposition tool provided by Yield Engineering Systems ("YES") with chemical vapor deposition process developed by Illumina, Inc. It include three different vapor deposition systems. The automated YES-VertaCoat silane vapor system is designed for volume production with a flexible wafer handling module that can accommodate 200 or 300 mm wafers. The manual load YES-1224P Silane Vapor System is designed for versatile volume production with its configurable large capacity chambers. Yes-LabKote is a low-cost, tabletop version that is ideal for feasibility studies and for R&D.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., $—CF_3$), halo($C_1$-$C_6$)alkoxy (e.g., $—OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo ($=O$). Wherever a group is described as "optionally substituted" that group can be substituted with the above substituents.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as $—CH_2—$, $—CH_2CH_2—$, $—CH_2CH(CH_3)CH_2—$, and the like. Other radical naming conventions clearly indicate that the radical is a di-radical such as "alkylene" or "alkenylene."

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

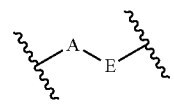

includes the substituent being oriented such that the A is attached at the leftmost attachment point of the molecule as well as the case in which A is attached at the rightmost attachment point of the molecule.

Where the compounds disclosed herein have at least one stereocenter, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

As used herein, the term "percent surface remaining" can refer to the intensity measured using a TET QC to stain the P5/P7 surface primers. The P5 and P7 primers are used on the surface of commercial flow cells sold by Illumina Inc. for sequencing on the HiSeq, MiSeq, Genome Analyzer and NextSeq platforms. The primer sequences are described in U.S. Pat. Pub. No. 2011/0059865 A1, which is incorporated herein by reference. TET is a dye labeled oligonucleotide having complimentary sequence to the P5/P7 primers. TET can be hybridized to the P5/P7 primers on a surface; the excess TET can be washed away, and the attached dye concentration can be measured by fluorescence detection using a scanning instrument such as a Typhoon Scanner (General Electric).

The skilled artisan will recognize that some structures described herein may be resonance forms or tautomers of compounds that may be fairly represented by other chemical structures; the artisan recognizes that such structures may only represent a very small portion of a sample of such compound(s). Such compounds are considered within the scope of the structures depicted, though such resonance forms or tautomers are not represented herein.

Silane or Silane Derivatives

Some embodiments disclosed herein relate to silane or silane derivatives comprising a plurality of unsaturated moieties selected from cycloalkenes, cycloalkynes, heterocycloalkenes, heterocycloalkynes or optionally substituted variants or combinations thereof. As used herein, "cycloalkene" means a carbocyclyl ring or ring system having at least one double bond, wherein no ring in the ring system is aromatic. As used herein, "heterocycloalkene" means a carbocyclyl ring or ring system contains at least one heteroatom in ring backbone, having at least one double bond, wherein no ring in the ring system is aromatic. As used herein, "cycloalkyne" means a carbocyclyl ring or ring system having at least one triple bond, wherein no ring in the ring system is aromatic. As used herein, "heterocycloalkyne" means a carbocyclyl ring or ring system contains at least one heteroatom in ring backbone, having at least one triple bond, wherein no ring in the ring system is aromatic. In some embodiments, the heteroatom in the heterocycloalkene is selected from the group consisting of N, O or S. Both cycloalkene and heterocycloalkene can be optionally substituted. The unsaturated moieties can be mono-valent or di-valent. The unsaturated moieties can be covalently attached either directly to the silion atoms of the silane or silane derivatives, or indirectly attached via linkers. The unsaturated moieties can be further bounded to a functionalized molecule. In some embodiments, the unsaturated moieties are optionally substituted cycloalkenes, such as norbornene and derivatives thereof. In some embodiments, the unsaturated moieties are optionally substituted cyclooctyne or bicyclononynes. Other cycloalkenes, heterocycloalkenes, cycloalkynes, heterocycloalkynes presenting ring strain can also be used as unsaturated moieties.

Norbornenes

In some embodiments, the cycloalkene is norbornene or a norbornene derivative.

In some embodiments, norbornene can be substituted with one or more substituents selected from selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —$CF_3$), halo($C_1$-$C_6$)alkoxy (e.g., —$OCF_3$), $C_1$-$C_6$alkylthio, arylthio, amino, amino($C_1$-$C_6$)alkyl, nitro, 0-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O).

Alternatively, the two adjacent substituents on norbornene can form additional rings. For example,

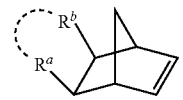

represents a di-substituted norbornene, wherein $R^a$ and $R^b$, together with the atom to which they are attached, can be joined together to form an optionally substituted aryl, an optionally substituted heteroaryl, an optionally substituted cycloalkyl or an optionally substituted heterocyclyl.

In some embodiments, norbornene can be replaced by other cycloalkenes. No limiting examples include optionally substituted trans-cyclooctene, optionally substituted trans-cyclopentene, optionally substituted trans-cycloheptene, optionally substituted trans-cyclononene, optionally substituted bicyclo[3.3.1]non-1-ene, optionally substituted bicyclo[4.3.1]dec-1(9)-ene, optionally substituted bicyclo[4.2.1]non-1(8)-ene, and optionally substituted bicyclo[4.2.1]-non-1-ene.

Hetero(Norbornenes)

In some embodiments, the heterocycloalkene used herein is a heteronorbornene. As used herein, (hetero)norbornene means one or more carbon atoms in a norbornene molecule in replaced by one or more heteroatoms. Non-limiting examples of (hetero)norbornene include

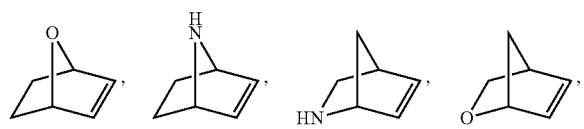

or optionally substituted variants thereof.

Exemplary Norbornene Reactions

A. 1,3-Dipolar Cycloaddition with Azides

The reaction of organic azides and olefinic bonds leading to the formation of 1,2,3-triazoline was first reported by Wolff in 1912. See Wolff, Liebigs. Ann., 1912, 394, 23. This type of reaction is termed as 1,3-dipolar cycloaddition. Azide additions to terminal alkyne were recognized as an example of 1,3-dipolar cycloaddition reaction from the research of Huisgen. See Proceedings of the Chemical Society, 1961, 357-396. Scheiner et al. reported the kinetic investigation of aryl azides to norbornene (see Scheiner et al., J. Am. Chem. Soc, 1965, 87, 306-311). The general reaction scheme is shown as follows:

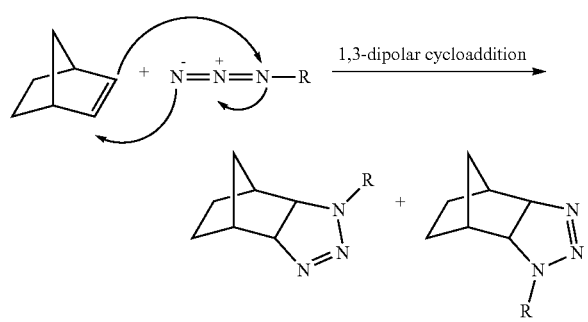

In addition, Shea et al. reported studies of reactivity of torsionally strained double bonds in 1,3-dipolar cycloadditions with 2,4,6-trinitrophenyl azide. A series of mono- and bi-cyclic olefins including trans-cycloalkenes and bridgehead alkenes were tested. See, Shea et al., J. Am. Chem. Soc. 1992, 114, 4846-4855.

B. Coupling Reaction with Tetrazines

The additive-free "click" reaction for polymer functionalization and coupling by the inverse electron demand Diels-Alder ($DA_{inv}$) reaction of tetrazine and norbornene was reported by Hansell et al. (see Hansell et al., J. Am. Chem. Soc. 2011, 133, 13828-13831). The general reaction scheme is shown as follows:

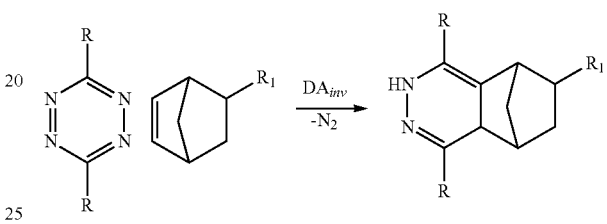

Other exemplary metal-free click reactions includes the (hetero-)Diels-Alder and the radical based thiol-ene reaction, as reported by Hoyle et al., Chem. Soc. Rev. 2010, 39, 1355-1387.

C. Coupling Reaction with Tetrazoles and Hydrazones

Kaya et al. reported a norbornene amino acid (1) for protein modification in a copper-free click reaction. See Kaya et al., Angew. Chem. Int. Ed. 2012, 51, 4466-4469. In the first example, a nitrile imine was generated by base-promoted HCl elimination from the hydrazonyl chloride and then used in a cycloaddition reaction with the norbornene derivative (1). In the second example, the nitrile imine was generated from a tetrazole in a photo-chemical reaction.

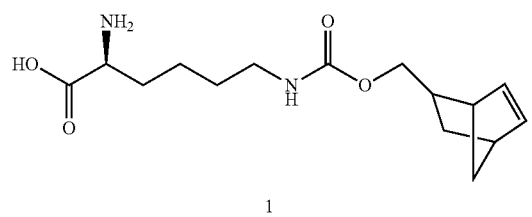

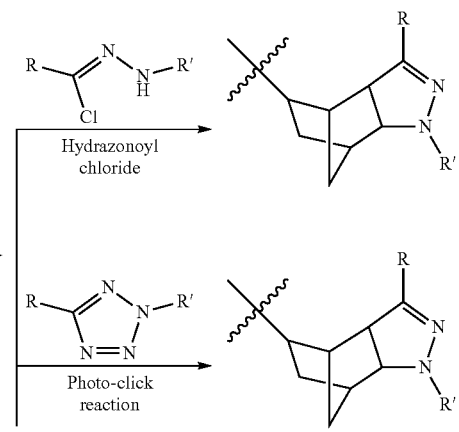

D. Ring-Opening Reactions with Olefins

Figure 10:
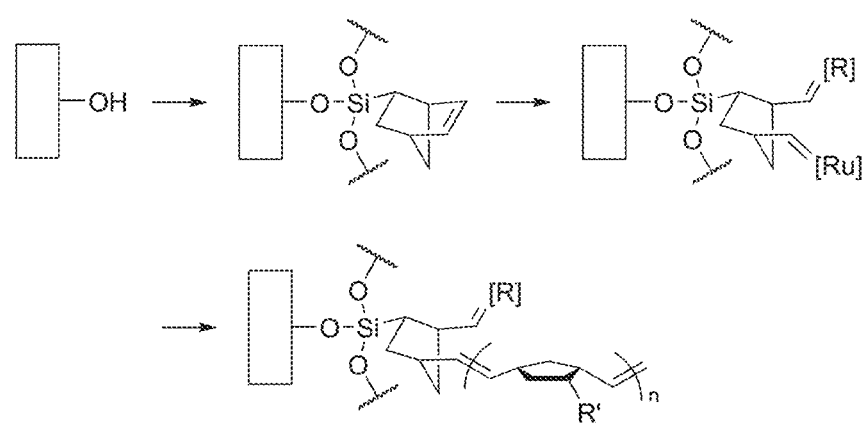
FIG. 10 shows a flow chart of growing thin polymer films from the surface of a silicon wafer.

Kim et al. reported a method for growing thin polymer films from the surface of a silicon wafer bearing a native oxide (Si/SiO$_2$) by using a surface-initiated ring-opening metathesis polymerization of norbornene. FIG. 10 outlines a three-step procedure: (i) the formation of a self-assembled monolayer on silicon that comprising norbornenyl groups; (ii) the attachment of a ruthenium catalyst [(Cy$_3$P)$_2$Cl$_2$Ru═CHPh, Cy=cyclohexyl] to the surface; and (iii) the polymerization of added monomers to generate the film. See Kim et al., *Macromolecules* 2000, 33, 2793-2795.

Similarly, Liu et al. reported the region-selective ring-opening/cross-metathesis reactions of norbornene derivatives with electron-rich olefins, catalyzed by a ruthenium catalyst, as shown in the scheme below. See Liu et al., *Org. Lett.* 2005, 7, 131-133.

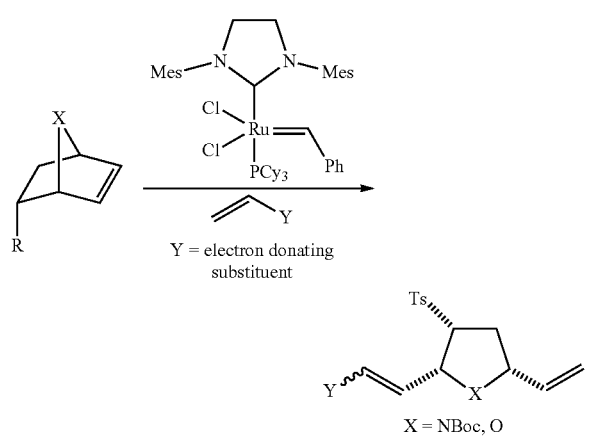

E. Cycloaddition with Nitrile Oxides

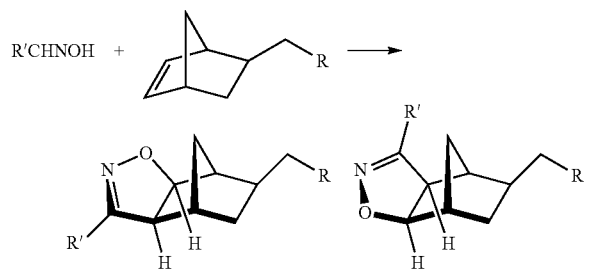

Gutsmiedl et al. reported the first examples of strain-promoted nitrile oxide cycloaddition involved norbornene-modified DNA substrate. The strained alkene is suited to cycloaddition with a variety of nitrile oxides generated in situ either from hydroxamoyl chlorides or directly by treatment of parent oxime with N-Chlorosuccinimide. See Gutsmiedl et al., *Org. Lett.* 2009, 11, 2405-2408.

Cyclooctyne

In some embodiments, the cycloalkyne is cyclooctyne or a cyclooctyne derivative.

In some embodiments, cycloalkyne can be substituted with one or more substituents selected from selected from C$_1$-C$_6$ alkyl, C$_1$-C$_6$ alkenyl, C$_1$-C$_6$ alkynyl, C$_1$-C$_6$ heteroalkyl, C$_3$-C$_7$ carbocyclyl (optionally substituted with halo, C$_1$-C$_6$ alkyl, C$_1$-C$_6$ alkoxy, C$_1$-C$_6$ haloalkyl, and C$_1$-C$_6$ haloalkoxy), C$_3$-C$_7$-carbocyclyl-C$_1$-C$_6$-alkyl (optionally substituted with halo, C$_1$-C$_6$ alkyl, C$_1$-C$_6$ alkoxy, C$_1$-C$_6$ haloalkyl, and C$_1$-C$_6$ haloalkoxy), 5-10 membered heterocyclyl (optionally substituted with halo, C$_1$-C$_6$ alkyl, C$_1$-C$_6$ alkoxy, C$_1$-C$_6$ haloalkyl, and C$_1$-C$_6$ haloalkoxy), 5-10 membered heterocyclyl-C$_1$-C$_6$-alkyl (optionally substituted with halo, C$_1$-C$_6$ alkyl, C$_1$-C$_6$ alkoxy, C$_1$-C$_6$ haloalkyl, and C$_1$-C$_6$ haloalkoxy), aryl (optionally substituted with halo, C$_1$-C$_6$ alkyl, C$_1$-C$_6$ alkoxy, C$_1$-C$_6$ haloalkyl, and C$_1$-C$_6$ haloalkoxy), aryl(C$_1$-C$_6$)alkyl (optionally substituted with halo, C$_1$-C$_6$ alkyl, C$_1$-C$_6$ alkoxy, C$_1$-C$_6$ haloalkyl, and C$_1$-C$_6$ haloalkoxy), 5-10 membered heteroaryl (optionally substituted with halo, C$_1$-C$_6$ alkyl, C$_1$-C$_6$ alkoxy, C$_1$-C$_6$ haloalkyl, and C$_1$-C$_6$ haloalkoxy), 5-10 membered heteroaryl(C$_1$-C$_6$) alkyl (optionally substituted with halo, C$_1$-C$_6$ alkyl, C$_1$-C$_6$ alkoxy, C$_1$-C$_6$ haloalkyl, and C$_1$-C$_6$ haloalkoxy), halo, cyano, hydroxy, C$_1$-C$_6$ alkoxy, C$_1$-C$_6$ alkoxy(C$_1$-C$_6$)alkyl (i.e., ether), aryloxy, sulfhydryl (mercapto), halo(C$_1$-C$_6$) alkyl (e.g., —CF$_3$), halo(C$_1$-C$_6$)alkoxy (e.g., —OCF$_3$), C$_1$-C$_6$alkylthio, arylthio, amino, amino(C$_1$-C$_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (═O).

Alternatively, the two adjacent substituents on cyclooctyne can form additional rings. For example,

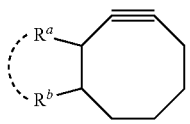

represents a di-substituted cyclooctyne, wherein R$^a$ and R$^b$, together with the atom to which they are attached, can be joined together to form an optionally substituted aryl, an optionally substituted heteroaryl, an optionally substituted cycloalkyl or an optionally substituted heterocyclyl. In some embodiments, the cyclooctyne derivative can comprise the following structures:

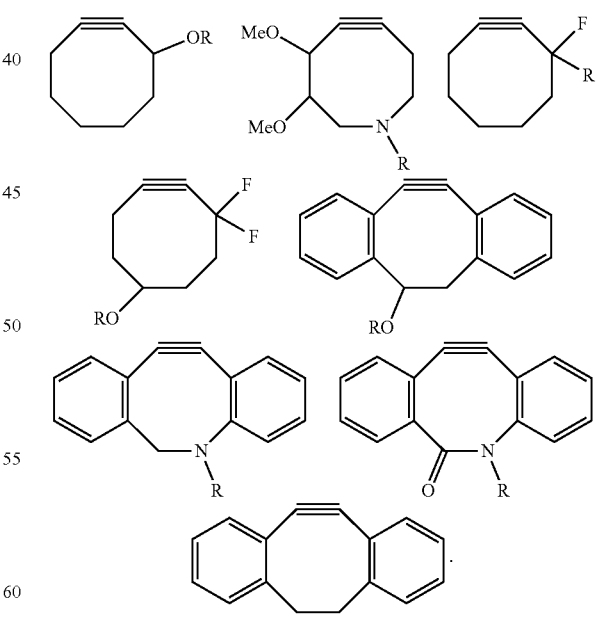

Strain-Promoted Azide-Alkyne Cycloaddition or Nitrile Oxide-Alkyne Cycloaddition Cyclooctynes can undergo 1,3-cycloaddition with azides. This type of strain-promoted azide-alkyne cycloaddition (SPAAC) reaction has been used in the copper-free DNA ligation. Van Geel et al., has reported that a variety of strained octynes can be used to efficiently label azide tagged proteins. See R. van Geel et al., "Preventing Thiol-yne Addition Improves the Specificity of Strain-Promoted Azide-Alkyne Cycloaddition," *Bioconjugate Chem.*, 2012, 23, 392-398. Similar work has also been reported by Yao et al. who has demonstrated that strained alkynes can be used to attach fluorophores to amino acide squences. See Yao et al, "Fluorophore targeting to cellular proteins via enzyme-mediated azide ligation and strain-promoted cycloaddition," *J. Am. Chem. Soc.*, 2012, 134, 3720-3728.

Recent studies on relative activity of nitrile oxides, nitrones as alternative to azide dipoles in reaction with cyclooctynes suggested superior reactivities for strain-promoted alkyne/nitrile oxide cycloaddition. See Sanders et al., *J. Am. Soc. Chem.* 2011, 133, 949-957; Jawalekar et al., *Chem. Commun.* 2011, 47, 3198-3200; and McKay et al., *Chem. Commun.* 2010, 46, 931-933. It was observed that the rate constant for [3+2] addition of bicyclo[6.1.0]nonyne (BCN) to benzonitrile oxide was greater by a factor of 10 than that overserved for the corresponding reaction with benzyl azide. Similar results were also observed with cycloaddition between dibenzocycloactynol (DIBO) and benzonitrile oxide (generated in situ from hydroxamoyl chloride) or benzyl azide. The study suggests the former reaction was about 60 times faster than the latter.

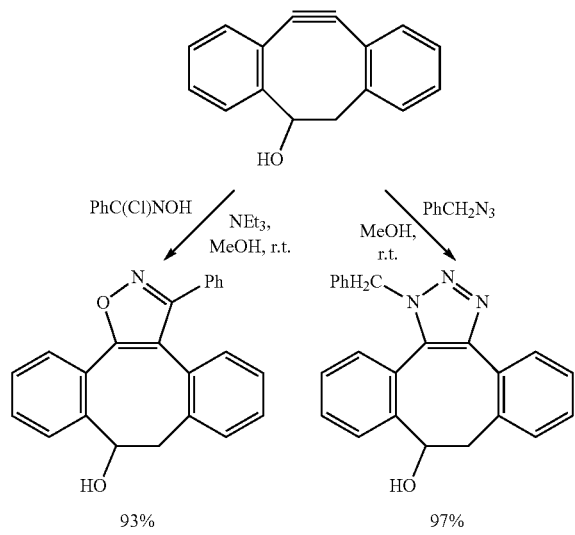

Bicyclononynes

In some embodiments, the cycloalkynes can comprise bicyclic ring system, for example, bicyclononynes. In some embodiments, the bicyclononynes can be selected from bicyclo[6.1.0]non-4-yne or derivatives thereof. In some other embodiments, the bicyclononynes can also be selected from bicyclo[6.1.0]non-2-yne or bicyclo[6.1.0]non-3-yne.

In some embodiments, bicyclononynes can be substituted with one or more substituents selected from selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —CF$_3$), halo($C_1$-$C_6$)alkoxy (e.g., —OCF$_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O).

Alternatively, the two adjacent substituents on a bicyclononyne can form additional rings. For example,

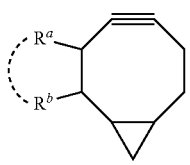

represents a di-substituted bicyclo[6.1.0]non-4-yne, wherein $R^a$ and $R^b$, together with the atom to which they are attached, can be joined together to form an optionally substituted aryl, an optionally substituted heteroaryl, an optionally substituted cycloalkyl or an optionally substituted heterocyclyl. Bicyclononynes can undergo similar SPAAC alkyne cycloaddition with azides or nitrile oxides as described above with respect to cyclooctyne due to the strain in the bicyclic ring system.

Hydrogels

Some embodiments described herein include immobilizing a functionalized hydrogel to a surface of a substrate via unsaturated moieties of the functionalized silane or silane derivatives. Non-limiting examples of hydrogels can be used in the present application are described herein.

WO 00/31148 discloses polyacrylamide hydrogels and polyacrylamide hydrogel-based arrays in which a so-called polyacrylamide prepolymer is formed, preferably from acrylamide and an acrylic acid or an acrylic acid derivative containing a vinyl group. Crosslinking of the prepolymer may then be affected. The hydrogels so produced are solid-supported, preferably on glass. Functionalization of the solid-supported hydrogel may also be effected.

WO 01/01143 describes technology similar to WO 00/31148 but differing in that the hydrogel bears functionality capable of participating in a [2+2] photocycloaddition reaction with a biomolecule so as to form immobilized arrays of such biomolecules. Dimethylmaleimide (DMI) is a particularly preferred functionality. The use of [2+2] photocycloaddition reactions, in the context of polyacrylamide-based microarray technology is also described in WO 02/12566 and WO 03/014392.

U.S. Pat. No. 6,465,178 discloses the use of reagent compositions in providing activated slides for use in preparing microarrays of nucleic acids; the reagent compositions include acrylamide copolymers. The activated slides are stated to be particularly well suited to replace conventional (e.g. silylated) glass slides in the preparation of microarrays.

WO 00/53812 discloses the preparation of polyacrylamide-based hydrogel arrays of DNA and the use of these arrays in replica amplification.

Once hydrogels have been formed, molecules may then be attached to them so as to produce molecular arrays, if desired. Attachment has been effected in different ways in the prior art. For example, U.S. Pat. No. 6,372,813 teaches immobilization of polynucleotides bearing dimethylmaleimide groups to the hydrogels produced which bear dimethylmaleimide groups by conducting a [2+2] photocycloaddition step between two dimethylmaleimide groups-one attached to the polynucleotide to be immobilized and one pendant from the hydrogel.

Where the molecular array is formed after generation of the hydrogel, two strategies have been employed to achieve this end. Firstly, the hydrogel may be modified chemically after it is produced. Problems with this approach include an overall low efficiency in the preparation of the array and the low stability relating to the attachment chemistry, particularly upon exposure to high temperatures, ionic solutions and multiple wash steps.

A more common alternative is to effect polymerization with a co-monomer having a functionality primed or pre-activated to react with the molecules to be arrayed.

Alternatives to initial formation of hydrogels followed by subsequent arraying of molecules thereto have been described in the prior art where the array is formed at the same time as the hydrogel is produced. This may be effected by, for example, direct copolymerization of acrylamide-derivatized polynucleotides. An example of this approach is described in WO 01/62982 in which acrylamide-derivatized polynucleotides are mixed with solutions, of acrylamide and polymerization is effected directly.

Mosaic Technologies (Boston, Mass., USA) produce ACRYDITE™ (an acrylamide phosphoramidite) which can be reacted with polynucleotides prior to copolymerization of the resultant monomer with acrylamide.

Efimov et al. (Nucleic Acids Research, 1999, 27 (22), 4416-4426) disclose a further example of a simultaneous formation of hydrogel/array in which copolymerization of acrylamide, reactive acrylic acid derivatives and the modified polynucleotides having 5'- or 3'-terminal acrylamide groups is affected.

Polymers

Some embodiments described herein include immobilizing a functionalized polymer to a surface of a substrate via cycloalkene or heterocycloalkene functionalized silane or silane derivatives. Non-limiting examples of the polymers that can be used in the present application are described in U.S. Ser. No. 13/784,368 and U.S. Pat. Pub. No. 2011/0059865, which are hereby incorporated by references in their entireties.

In some embodiments, the polymer used herein comprises a recurring unit of Formula (I) and a recurring unit of Formula (II):

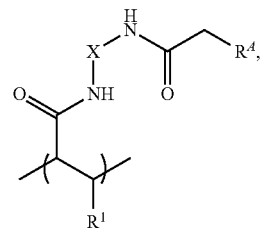

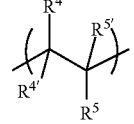

wherein: $R^1$ is H or alkyl; $R^4$ is selected from the group consisting of azido, optionally substituted amino, optionally substituted alkenyl, optionally substituted hydrazone, optionally substituted hydrazine, carboxyl, hydroxy, optionally substituted tetrazole, optionally substituted tetrazine, and thiol; X is an optionally substituted alkylene linker or an optionally substituted heteroalkylene linker; $R^4$, $R^{4'}$, $R^5$ and $R^{5'}$ are each independently selected from H, $R^6$, $OR^6$, —C(O)$OR^6$, —C(O)$R^6$, —OC(O)$R^6$, —C(O) $NR^7R^8$, or —$NR^7R^8$; $R^6$ is independently selected from H, OH, alkyl, cycloalkyl, hydroxyalkyl, aryl, heteroaryl, heterocyclyl, or optionally substituted variants thereof; $R^7$ and $R^8$ are each independently selected from H or alkyl, or $R^7$ and $R^8$ are joined together with the atom or atoms to which they are attached to form a heterocycle.

In some embodiments, $R^4$ is azido. In some embodiments, X is an optionally substituted alkylene linker. In some embodiments, $R^1$ is hydrogen. In some other embodiments, $R^1$ is methyl. In some embodiments, $R^4$ is hydrogen and $R^{4'}$ is —C(O)$NR^7R^8$. In some embodiments, each of $R^5$ and $R^{5'}$ is hydrogen. In some embodiments, $R^5$ is hydrogen and $R^{5'}$ is methyl.

In some embodiment, the polymer used herein comprises a polymer of Formula (III) or (III'):

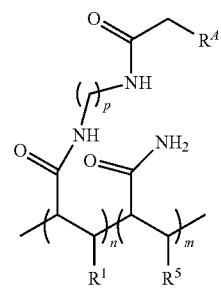

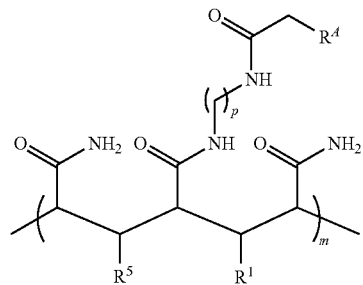

wherein $R^1$ is selected from H or optionally substituted alkyl; $R^4$ is selected from the group consisting of azido, optionally substituted amino, optionally substituted alkenyl, optionally substituted hydrazone, optionally substituted hydrazine, carboxyl, hydroxy, optionally substituted tetrazole, optionally substituted tetrazine, and thiol; each of the —(CH$_2$)-p can be optionally substituted; p is an integer in the range of 1-50; $R^5$ is selected from H or optionally substituted alkyl; n is an integer in the range of 1 to 50,000; and m is an integer in the range of 1 to 100,000. In some embodiments, p is 5. In some embodiments, $R^4$ is azido.

PAZAM

In one embodiment, the polymer of Formula (III) or (III') is also represented by Formula (IIIa) or (IIIb):

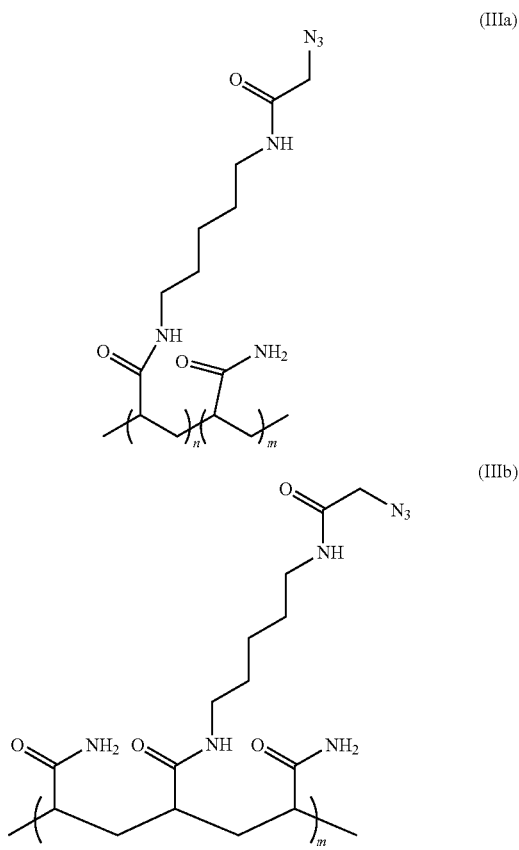

wherein n is an integer in the range of 1-20,000, and m is an integer in the range of 1-100,000.

In some embodiments, the functionalized molecule used for direct conjugation is poly(N-(5-azidoacetamidylpentyl) acrylamide-co-acrylamide) (PAZAM). In some embodiments, PAZAM is a linear polymer. In some other embodiments, PAZAM is a lightly cross-linked polymer. In some embodiments, PAZAM is applied to the surface as an aqueous solution. In some other embodiments, PAZAM is applied to the surface as an aqueous solution with one or more solvent additives, such as ethanol. The method for preparation different PAZAM polymers is discussed in detail in U.S. Ser. No. 13/784,368, which is hereby incorporated by reference in its entirety.

Substrates

In some embodiments, substrates used in the present application include silica-based substrates, such as glass, fused silica and other silica-containing materials. In some embodiments, silica-based substrates can also be silicon, silicon dioxide, silicon nitride, silicone hydrides. In some embodiments, substrates used in the present application include plastic materials such as polyethylene, polystyrene, poly(vinyl chloride), polypropylene, nylons, polyesters, polycarbonates and poly(methyl methacrylate). Preferred plastics material are poly(methyl methacrylate), polystyrene and cyclic olefin polymer substrates. In some embodiments, the substrate is a silica-based material or plastic material. In one embodiment, the substrate has at least one surface comprising glass.

In some other embodiments, the substrates can be a metal. In some such embodiments, the metal is gold. In some embodiments, the substrate has at least one surface comprising a metal oxide. In one embodiment, the surface comprises a tantalum oxide.

Acrylamide, enone, or acrylate may also be utilized as a substrate material. Other substrate materials can include, but are not limited to gallium arsenide, indium phosphide, aluminum, ceramics, polyimide, quartz, resins, polymers and copolymers. The foregoing lists are intended to be illustrative of, but not limited to the present application.

In some embodiments, the substrate and/or the substrate surface can be quartz. In some other embodiments, the substrate and/or the substrate surface can be semiconductor, i.e. GaAs or ITO.

Substrates can comprise a single material or a plurality of different materials. Substrates can be composites or laminates. Substrate can be flat, round, textured and patterned. Patterns can be formed, for example, by metal pads that form features on non-metallic surfaces, for example, as described in U.S. patent application Ser. No. 13/661,524, which is incorporated herein by reference. Another useful patterned surface is one having well features formed on a surface, for example, as described in U.S. Ser. No. 13/787,396, US Pat. App. Pub. No. 2011/0172118 A1 or U.S. Pat. No. 7,622,294, each of which is incorporated herein by reference. For embodiments that use a patterned substrate, a gel can be selectively attached to the pattern features (e.g. gel can be attached to metal pads or gel can be attached to the interior of wells) or alternatively the gel can be uniformly attached across both the pattern features and the interstitial regions.

Advantages in using plastics-based substrates in the preparation and use of molecular arrays include cost: the preparation of appropriate plastics-based substrates by, for example injection-molding, is generally cheaper than the preparation, e.g. by etching and bonding, of silica-based substrates. Another advantage is the nearly limitless variety of plastics allowing fine-tuning of the optical properties of the support to suit the application for which it is intended or to which it may be put.

Where metals are used as substrates or as pads on a substrate, this may be because of the desired application: the conductivity of metals can allow modulation of the electric field in DNA-based sensors. In this way, DNA mismatch discrimination may be enhanced, the orientation of immobilized oligonucleotide molecules can be affected, or DNA hybridization kinetics can be accelerated.

Preferably the substrate is silica-based but the shape of the substrate employed may be varied in accordance with the application for which the present application is practiced. Generally, however, slides of support material, such as silica, e.g. fused silica, are of particular utility in the preparation and subsequent integration of molecules. Of particular use in the practice of the present application are fused silica slides sold under the trade name SPECTROSIL™. This notwithstanding, it will be evident to the skilled person that the present application is equally applicable to other presentations of substrate (including silica-based supports), such as beads, rods and the like.

In some embodiments, the surface of the substrate comprises both functional molecules-coated regions and inert regions with no coatings. In some such embodiments, the functionalized molecule coatings are hydrogel or polymer coatings. The functional molecules-coated regions can comprise reactive sites, and thus, can be used to attach molecules through chemical bonding or other molecular interactions. In some embodiments, the functional molecules-coated regions (e.g. reactive features, pads, beads or wells) and the inert regions (referred to as interstitial regions) can alternate so as to form a pattern or a grid. Such patterns can be in one or two dimensions. In some embodiments, the inert regions can be selected from glass regions, metal regions, mask regions or interstitial regions, or combinations thereof. Alternatively these materials can form reactive regions. Inertness or reactivity will depend on the chemistry and processes used on the substrate. In one embodiment, the surface comprises glass regions. In another embodiment, the surface comprises metal regions. In still another embodiment, the surface comprises mask regions. In some embodiments of the compositions described herein, the substrate can be a bead. Non-limiting exemplary substrate materials that can be coated with a polymer of the present disclosure or that can otherwise be used in a composition or method set forth herein are described in U.S. Ser. Nos. 13/492,661 and 13/661,524, each of which is incorporated herein by reference.

In some embodiments, a substrate described herein is forms at least part of a flow cell or is located in a flow cell. In some such embodiments, the flow cells further comprise polynucleotides attached to the surface of the substrate via the functional molecules coating, for example, a polymer coating. In some embodiments, the polynucleotides are present in the flow cells in polynucleotide clusters, wherein the polynucleotides of the polynucleotide clusters are attached to a surface of the flow cell via the polymer coating. In such embodiments, the surface of the flow cell body to which the polynucleotides are attached is considered the substrate. In other embodiments, a separate substrate having a polymer coated surface is inserted into the body of the flow cell. In preferred embodiments, the flow cell is a flow chamber that is divided into a plurality of lanes or a plurality of sectors, wherein one or more of the plurality of lanes or plurality of sectors comprises a surface that is coated with a covalently attached polymer coating described herein. In some embodiments of the flow cells described herein, the attached polynucleotides within a single polynucleotide cluster have the same or similar nucleotide sequence. In some embodiments of the flow cells described herein, the attached polynucleotides of different polynucleotide clusters have different or nonsimilar nucleotide sequences. Exemplary flow cells and substrates for manufacture of flow cells that can be used in method or composition set forth herein include, but are not limited to, those commercially available from Illumina, Inc. (San Diego, CA) or described in US 2010/0111768 A1 or US 2012/0270305, each of which is incorporated herein by reference.

Silica-Based Substrate

In some embodiments, the substrates used in the present application are silica-based substrates. In general, silica-based substrate surface is chemically modified in some way so as to attach covalently a chemically reactive group capable of reacting with the functionalized molecules, for example, hydrogel, polymer or a partially formed hydrogel (e.g. a prepolymer (PRP)). The surface-activating agent is typically an organosilane compound. In one embodiment, the surface-activating agent is 7-methacryloxypropylt-rimethoxysilane, known as "Bind Silane" or "Crosslink Silane" and commercially available from Pharmacia, although other silicon-based surface-activating agents are also known, such as monoethoxydimethylsilylbutanal, 3-mercaptopropyl-trimethoxysilane and 3-aminopropylt-rimethoxysilane (all available from Aldrich). In this way, pendant functional groups such as amine groups, aldehydro groups or polymerizable groups (e.g. olefins) may be attached to the silica.

The present application employs organosilane compounds comprising covalently attached cycloalkenes or heterocycloalkenes. In some embodiments, the cycloalkene is an optionally substituted norbornene. In some embodiments, the silane moiety of the organosilane compounds has the following structure:

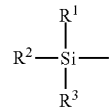

wherein $R^1$, $R^2$ and $R^3$ are each independently selected from hydrogen, halogen, optionally substituted alkyl, optionally substituted alkoxy, optionally substituted aryl, optionally substituted aryloxy, optionally substituted heteroaryl or optionally substituted heteroaryloxy. In some such embodiments, $R^1$, $R^2$ and $R^3$ are independently optionally substituted alkoxy. In some further embodiments, each of $R^1$, $R^2$ and $R^3$ is methoxy. In one embodiment, the organosilane compound is [(5-bicyclo[2.2.1]hept-2-enyl)ethyl]trimethoxysilane.

Linker

In some embodiments described herein, the linker between the silane or silane derivative and the cycloalkene or heterocycloalkene is selected from an optionally substituted alkylene, an optionally substituted heteroalkylene, an optionally substituted cycloalkylene, an optionally substituted heterocyclylene, an optionally substituted arylene, an optionally substituted heteroarylene, an optionally substituted polyethylene glycol, a cleavable linker, or combination thereof.

In some embodiments, the linker described herein is an optionally substituted alkylene linker. In some embodiment, the linker is —(CH$_2$)n-, wherein n is selected from 1 to 20,000. In one embodiment, n is 2. In some other embodiments, the linker described herein is an optionally substituted heteroalkylene linker. For example, the linker is —(CH$_2$)n-, wherein n is selected from 1 to 20,000, and one or more of the carbon atoms on the skeleton is replaced by one or more heteroatoms selected from O, S, N or P.

In some embodiments, the linker described herein is a cleavable linker. In some embodiments, the linker is selected from acid labile linkers (including dialkoxybenzyl linkers, Sieber linkers, indole linkers, t-butyl Sieber linkers), electrophilically cleavable linkers, nucleophilically cleavable linkers, photocleavable linkers, cleavage under reductive conditions, oxidative conditions, cleavage via use of safety-catch linkers, and cleavage by elimination mechanisms. In some such embodiments, $L^A$ is selected from a disulfide linker (—S—S—), ester, nitrobenzene, imine, enzymatically or chemically cleavable peptide and polynucleotide, such as DNA.

Cleavable linkers are known in the art, and conventional chemistry can be applied to attach a linker to a nucleotide base and a label. The linker can be cleaved by any suitable method, including exposure to acids, bases, nucleophiles, electrophiles, radicals, metals, reducing or oxidizing agents, light, temperature, enzymes etc. The linker as discussed herein may also be cleaved with the same catalyst used to cleave the 3'-O-protecting group bond. Suitable linkers can be adapted from standard chemical protecting groups, as disclosed in Greene & Wuts, Protective Groups in Organic Synthesis, John Wiley & Sons., or in Greg T. Hermanson's "Bioconjugate Techniques", Academic Press. Further suitable cleavable linkers used in solid-phase synthesis are disclosed in Guillier et al. (*Chem. Rev.* 100:2092-2157, 2000).

The use of the term "cleavable linker" is not meant to imply that the whole linker is required to be removed from, e.g., the reactive heterocycle. As an example, the cleavage site can be located at a position on the linker that ensures that part of the linker remains attached to the heterocycle after cleavage.

A. Electrophilically Cleaved Linkers

Electrophilically cleaved linkers are typically cleaved by protons and include cleavages sensitive to acids. Suitable linkers include the modified benzylic systems such as trityl, p-alkoxybenzyl esters and p-alkoxybenzyl amides. Other suitable linkers include tert-butyloxycarbonyl (Boc) groups and the acetal system.

The use of thiophilic metals, such as nickel, silver or mercury, in the cleavage of thioacetal or other sulfur-containing protecting groups can also be considered for the preparation of suitable linker molecules.

B. Nucleophilically Cleaved Linkers

Nucleophilic cleavage is also a well-recognized method in the preparation of linker molecules. Groups such as esters that are labile in water (i.e., can be cleaved simply at basic pH) and groups that are labile to non-aqueous nucleophiles, can be used. Fluoride ions can be used to cleave silicon-oxygen bonds in groups such as triisopropyl silane (TIPS) or t-butyldimethyl silane (TBDMS).

C. Photocleavable Linkers

Photocleavable linkers have been used widely in carbohydrate chemistry. It is preferable that the light required to activate cleavage does not affect the other components of the modified nucleotides. For example, if a fluorophore is used as the label, it is preferable if this absorbs light of a different wavelength to that required to cleave the linker molecule. Suitable linkers include those based on O-nitrobenzyl compounds and nitroveratryl compounds. Linkers based on benzoin chemistry can also be used (Lee et al., *J. Org. Chem.* 64:3454-3460, 1999).

D. Cleavage Under Reductive Conditions

There are many linkers known that are susceptible to reductive cleavage. Catalytic hydrogenation using palladium-based catalysts has been used to cleave benzyl and benzyloxycarbonyl groups. Disulfide bond reduction is also known in the art.

E. Cleavage Under Oxidative Conditions

Oxidation-based approaches are well known in the art. These include oxidation of p-alkoxybenzyl groups and the oxidation of sulfur and selenium linkers. The use of aqueous iodine to cleave disulfides and other sulfur or selenium-based linkers is also within the scope of the present application.

F. Safety-Catch Linkers

Safety-catch linkers are those that cleave in two steps. In a preferred system the first step is the generation of a reactive nucleophilic center followed by a second step involving an intra-molecular cyclization that results in cleavage. For example, levulinic ester linkages can be treated with hydrazine or photochemistry to release an active amine, which can then be cyclized to cleave an ester elsewhere in the molecule (Burgess et al., J. Org. Chem. 62:5165-5168, 1997).

G. Cleavage by Elimination Mechanisms

Elimination reactions can also be used. For example, the base-catalyzed elimination of groups such as Fmoc and cyanoethyl, and palladium-catalyzed reductive elimination of allylic systems, can be used.

In some embodiments, the linker can comprise a spacer unit. Other exemplary suitable cleavable linkers are discussed in details in U.S. Publication No. 2006-0188901, which is hereby incorporated by reference in its entirety.

Sequencing Application

A method set forth herein can use any of a variety of amplification techniques. Exemplary techniques that can be used include, but are not limited to, polymerase chain reaction (PCR), rolling circle amplification (RCA), multiple displacement amplification (MDA), or random prime amplification (RPA). In particular embodiments, one or more primers used for amplification can be attached to a polymer coating. In PCR embodiments, one or both of the primers used for amplification can be attached to a polymer coating. Formats that utilize two species of attached primer are often referred to as bridge amplification because double stranded amplicons form a bridge-like structure between the two attached primers that flank the template sequence that has been copied. Exemplary reagents and conditions that can be used for bridge amplification are described, for example, in U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2004/0002090; U.S. Patent Publ. No. 2007/0128624; and U.S. Patent Publ. No. 2008/0009420, each of which is incorporated herein by reference. PCR amplification can also be carried out with one of the amplification primers attached to a polymer coating and the second primer in solution. An exemplary format that uses a combination of one attached primer and soluble primer is emulsion PCR as described, for example, in Dressman et al., *Proc. Natl. Acad. Sci. USA* 100:8817-8822 (2003), WO 05/010145, or U.S. Patent Publ. Nos. 2005/0130173 or 2005/0064460, each of which is incorporated herein by reference. Emulsion PCR is illustrative of the format and it will be understood that for purposes of the methods set forth herein the use of an emulsion is optional and indeed for several embodiments an emulsion is not used. Furthermore, primers need not be attached directly to substrate or solid supports as set forth in the ePCR references and can instead be attached to a polymer coating as set forth herein.

RCA techniques can be modified for use in a method of the present disclosure. Exemplary components that can be used in an RCA reaction and principles by which RCA produces amplicons are described, for example, in Lizardi et al., *Nat. Genet.* 19:225-232 (1998) and US 2007/0099208 A1, each of which is incorporated herein by reference. Primers used for RCA can be in solution or attached to a polymer coating.

MDA techniques can be modified for use in a method of the present disclosure. Some basic principles and useful conditions for MDA are described, for example, in Dean et al., *Proc Natl. Acad. Sci. USA* 99:5261-66 (2002); Lage et al., *Genome Research* 13:294-307 (2003); Walker et al., *Molecular Methods for Virus Detection*, Academic Press, Inc., 1995; Walker et al., *Nucl. Acids Res.* 20:1691-96 (1992); U.S. Pat. Nos. 5,455,166; 5,130,238; and 6,214,587, each of which is incorporated herein by reference. Primers used for MDA can be in solution or attached to a polymer coating.

In particular embodiments a combination of the above-exemplified amplification techniques can be used. For example, RCA and MDA can be used in a combination wherein RCA is used to generate a concatameric amplicon in solution (e.g. using solution-phase primers). The amplicon can then be used as a template for MDA using primers that are attached to a polymer coating. In this example, amplicons produced after the combined RCA and MDA steps will be attached to the polymer coating.

In some embodiments, the functionalized hydrogel or polymer-coated substrate described herein can be used for determining a nucleotide sequence of a polynucleotide. In such embodiments, the method can comprise the steps of (a) contacting a polynucleotide polymerase with polynucleotide clusters attached to a surface of a substrate via any one of the polymer or hydrogel coatings described herein; (b) providing nucleotides to the polymer-coated surface of the substrate such that a detectable signal is generated when one or more nucleotides are utilized by the polynucleotide polymerase; (c) detecting signals at one or more polynucleotide clusters; and (d) repeating steps (b) and (c), thereby determining a nucleotide sequence of a polynucleotide present at the one or more polynucleotide clusters.

Nucleic acid sequencing can be used to determine a nucleotide sequence of a polynucleotide by various processes known in the art. In a preferred method, sequencing-by-synthesis (SBS) is utilized to determine a nucleotide sequence of a polynucleotide attached to a surface of a substrate via any one of the polymer coatings described herein. In such process, one or more nucleotides are provided to a template polynucleotide that is associated with a polynucleotide polymerase. The polynucleotide polymerase incorporates the one or more nucleotides into a newly synthesized nucleic acid strand that is complementary to the polynucleotide template. The synthesis is initiated from an oligonucleotide primer that is complementary to a portion of the template polynucleotide or to a portion of a universal or non-variable nucleic acid that is covalently bound at one end of the template polynucleotide. As nucleotides are incorporated against the template polynucleotide, a detectable signal is generated that allows for the determination of which nucleotide has been incorporated during each step of the sequencing process. In this way, the sequence of a nucleic acid complementary to at least a portion of the template polynucleotide can be generated, thereby permitting determination of the nucleotide sequence of at least a portion of the template polynucleotide. Flow cells provide a convenient format for housing an array that is produced by the methods of the present disclosure and that is subjected to a sequencing-by-synthesis (SBS) or other detection technique that involves repeated delivery of reagents in cycles. For example, to initiate a first SBS cycle, one or more labeled nucleotides, DNA polymerase, etc., can be flowed into/through a flow cell that houses a nucleic acid array made by methods set forth herein. Those sites of an array where primer extension causes a labeled nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with an array produced by the methods of the present disclosure are described, for example, in Bentley et al., *Nature* 456: 53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference in its entirety.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., *Analytical Biochemistry* 242(1), 84-9 (1996); Ronaghi, *Genome Res.* 11(1), 3-11 (2001); Ronaghi et al. *Science* 281(5375), 363 (1998); U.S. Pat. Nos. 6,210,891; 6,258,568 and 6,274,320, each of which is incorporated herein by reference in its entirety). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be used for application of pyrosequencing to arrays of the present disclosure are described, for example, in WO 12/058096 A1, US 2005/0191698 A1, U.S. Pat. Nos. 7,595,883, and 7,244,559, each of which is incorporated herein by reference in its entirety.

Sequencing-by-ligation reactions are also useful including, for example, those described in Shendure et al. *Science* 309:1728-1732 (2005); U.S. Pat. Nos. 5,599,675; and 5,750,341, each of which is incorporated herein by reference in its entirety. Some embodiments can include sequencing-by-hybridization procedures as described, for example, in Bains et al., *Journal of Theoretical Biology* 135(3), 303-7 (1988); Drmanac et al., *Nature Biotechnology* 16, 54-58 (1998); Fodor et al., *Science* 251(4995), 767-773 (1995); and WO 1989/10977, each of which is incorporated herein by reference in its entirety. In both sequencing-by-ligation and sequencing-by-hybridization procedures, nucleic acids that are present at sites of an array are subjected to repeated cycles of oligonucleotide delivery and detection. Fluidic systems for SBS methods as set forth herein or in references cited herein can be readily adapted for delivery of reagents for sequencing-by-ligation or sequencing-by-hybridization procedures. Typically, the oligonucleotides are fluorescently labeled and can be detected using fluorescence detectors similar to those described with regard to SBS procedures herein or in references cited herein.

Some embodiments can utilize methods involving the real-time monitoring of DNA polymerase activity. For example, nucleotide incorporations can be detected through fluorescence resonance energy transfer (FRET) interactions between a fluorophore-bearing polymerase and 7-phosphate-labeled nucleotides, or with zeromode waveguides (ZMWs). Techniques and reagents for FRET-based sequencing are described, for example, in Levene et al. Science 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference in its entirety.

Some SBS embodiments include detection of a proton released upon incorporation of a nucleotide into an extension product. For example, sequencing based on detection of released protons can use an electrical detector and associated techniques that are commercially available from Ion Torrent (Guilford, CT, a Life Technologies subsidiary) or sequencing methods and systems described in US 2009/0026082 A1; US 2009/0127589 A1; US 2010/0137143 A1; or US 2010/0282617 A1, each of which is incorporated herein by reference in its entirety.

Another useful application for an array of the present disclosure, for example, having been produced by a method set forth herein, is gene expression analysis. Gene expression can be detected or quantified using RNA sequencing techniques, such as those, referred to as digital RNA sequencing. RNA sequencing techniques can be carried out using sequencing methodologies known in the art such as those set forth above. Gene expression can also be detected or quantified using hybridization techniques carried out by direct hybridization to an array or using a multiplex assay, the products of which are detected on an array. An array of the present disclosure, for example, having been produced by a method set forth herein, can also be used to determine genotypes for a genomic DNA sample from one or more individual. Exemplary methods for array-based expression and genotyping analysis that can be carried out on an array of the present disclosure are described in U.S. Pat. Nos. 7,582,420; 6,890,741; 6,913,884 or 6,355,431 or US Pat. Pub. Nos. 2005/0053980 A1; 2009/0186349 A1 or US 2005/0181440 A1, each of which is incorporated herein by reference in its entirety.

In some embodiments of the above-described method which employ a flow cell, only a single type of nucleotide is present in the flow cell during a single flow step. In such embodiments, the nucleotide can be selected from the group consisting of dATP, dCTP, dGTP, dTTP and analogs thereof. In other embodiments of the above-described method which employ a flow cell, a plurality different types of nucleotides are present in the flow cell during a single flow step. In such methods, the nucleotides can be selected from dATP, dCTP, dGTP, dTTP and analogs thereof.

Determination of the nucleotide or nucleotides incorporated during each flow step for one or more of the polynucleotides attached to the polymer coating on the surface of the substrate present in the flow cell is achieved by detecting a signal produced at or near the polynucleotide template. In some embodiments of the above-described methods, the detectable signal comprises and optical signal. In other embodiments, the detectable signal comprises a non-optical signal. In such embodiments, the non-optical signal comprises a change in pH at or near one or more of the polynucleotide templates.

EXAMPLES

Additional embodiments are disclosed in further detail in the following examples, which are not in any way intended to limit the scope of the claims.

Example 1

Immobilization of PAZAM on Norbornene 1a Silanized Glass Surface

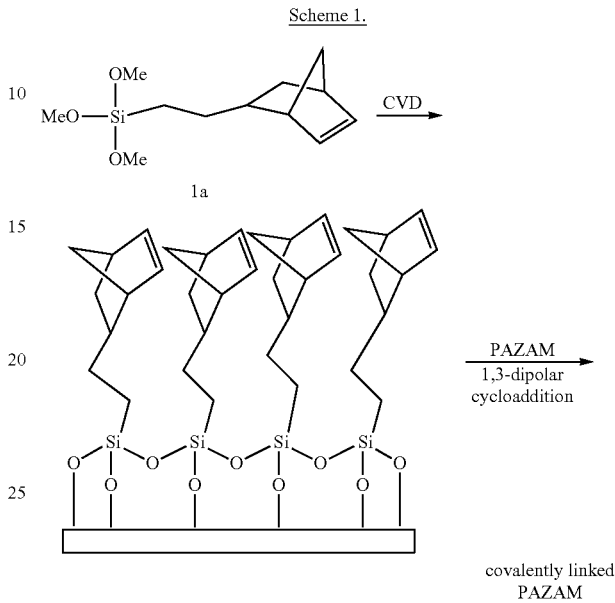

Surface Silanization

Method 1 (silanization using glass vacuum desiccator): 200 µL-500 µL of liquid norbornene silane were deposited inside a glass vial and placed inside a glass vacuum desiccator. Glass substrates were also placed inside the desiccator. The desiccator was then evacuated to a pressure of 15-30 mTorr, and placed inside an oven at a temperature between 60-125° C. Silanization was let to proceed for 1 h, after which the desiccator was removed from the oven, cooled and vented in air. The substrates were utilized right after this step, or they were subjected to an additional curing step (1 h at 100° C.) and/or a solvent wash step, such as an ethanol rinse.

Method 2 (silanization using YES CVD oven): First, substrates were introduced in the CVD oven chamber and the chamber was evacuated to a pressure of 300 mTorr. The samples were initially treated with an oxygen plasma for 10 min. After plasma activation, the chamber was evacuated, and a 10 min rehydration cycle was executed by injecting 0.5 mL of water at a base pressure of 500 mTorr. After an additional purging cycle, the silanization program was executed. After a 15 mins delay time, the silane valve was set to open for 0.15 sec, and to close for 20 sec. Silanization was performed at a base pressure of 500 mTorr and at a chamber temperature of 125° C. for 60 min, and followed by 2 nitrogen purge cycles, also at 125° C. The chamber was then vented over 3 min. The silanization cycle of the YES oven was highly automated and controlled. During the silanization step, the norbornene silane vessel was kept at 120° C. and the silane vapor lines were kept at a constant 125° C. The vacuum lines were kept at 145° C. After the cycle was completed, the substrates were removed, cooled outside the oven for a brief period and subsequently used without additional work-up. These substrates were viable for at least a month post-silanization.

PAZAM Deposition and Surface Crosslinking

500 µL of aqueous PAZAM (0.25%+5% ethanol) were deposited on top of a norbornene silanized glass substrate and spread across the surface. A thin film of PAZAM was obtained via spin coating with the following procedure: Step 1-600 rpm, 5 sec, acceleration 1500 rpm/sec; Step 2-1500 rpm, 30 sec, acceleration 5000 rpm/sec; Step 3-4000 rpm, 5 sec, acceleration 5000 rpm/sec; Step 4-600 rpm, 5 sec, acceleration 5000 rpm/sec. Other spin coat recipes can also be used. After spin-coating, the substrates were heated at 65-75° C. in oven or hot plate for 1 h.

Wash-Off: After the heating step, the substrates can be washed in water to remove the unbound PAZAM by adding a sonication step (10 min) at 45° C., followed by extensive water rinse and drying with a nitrogen gun.

Primer grafting: the substrate prepared was used in the primer grafting step by reacting alkyne oligonucleotides in KPi (10 mM) with PMDETA, copper sulfate and NaAsc (500 mg/mL aqueous solution) at 60° C. for 30 minutes.

QC: After primer grafting step is completed, the grafted primers were subjected to the TET quality control. TET is a dye labeled oligonucleotide having complimentary sequence to the P5/P7 primer. TET can be hybridized to the P5/P7 primer on a surface; the excess TET can be washed away, and the attached dye concentration can be measured by fluorescence detection using a scanning instrument such as a Typhoon Scanner (General Electric). The intensity of the dye concentration was measured as an indication of the percent surface remaining after the hydrogel immobilization. The PAZAM deposition and surface crosslinking procedures were also disclosed in U.S. application Ser. No. 13/784,368, which is incorporated by reference in its entirety.

Figure 1B:
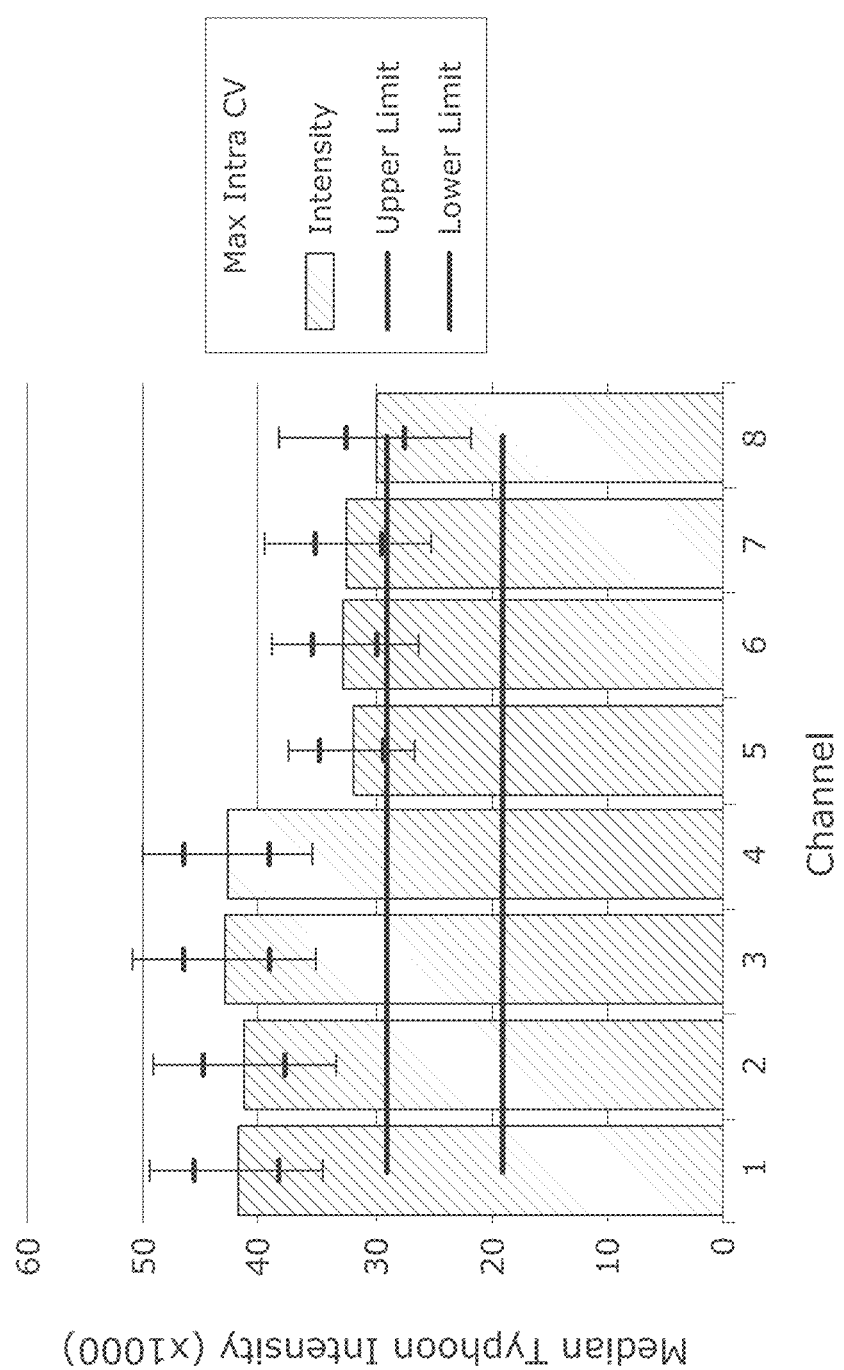
FIG. 1B shows the related chart of median Typhoon intensity of the grafted norbornene silane derivative (1a) silanized/PAZAM coated unpatterned surface hybridized with a complimentary TET dye-containing oligonucleotide sequence.

FIG. 1A shows a D263 Schott glass substrate silanized with the norbornene-silane derivative [(5-bicycle[2.2.1]hept-2-enyl)ethyl]trimethoxysilane (1a) and subsequently coated and thermally cross-linked with PAZAM. The dark area is the actual fluorescence intensity observed upon grafting P5/P7 primers and hybridizing with a TET-dye derivatized complementary strands. FIG. 1B shows the related chart of median fluorescence intensities for each lane of the same grafted norbornene (1a) silanized/PAZAM coated unpatterned surface hybridized with a complimentary TET dye-containing oligonucleotide sequence.

Example 2

Preparation of Patterned Surface with PAZAM on Nanowell Substrate

Patterned, sequenceable clusters were created by integrating the nanowell substrates with the PAZAM polymer and chemical mechanical polishing (CMP). A nanowell substrate (400 nm diameter 750 nm pitch, 300 nm depth well) was fabricated via a proprietary nanofabrication processed developed by Illumina and outsourced to Taiwan Semiconductor Manufacturing Company Ltd (TSMC) using nanoimprint lithography. Norbornene silane of Example 1 was deposited by CVD on the entire surface of the substrate and PAZAM was spin coated and heated at 60-70° C., creating a covalent linkage of the polymer to the substrate surface.

The interstitial covalently linked polymer was removed by polishing the surface with 10 wt % 3 µm $SiO_2$ micro particle slurry in water, through the CMP process. The patterned polymer substrate was then grafted with primers following standard Illumina protocol. The patterned primers on the substrate were imaged with a Typhoon imager. The substrate was then seeded with phiX DNA, clustered with Illumina's proprietary amplification protocol, derived from the Twist DX kit (isothermal amplification) and sequenced. Sequencing was conducted on an Illumina HiSeq 2000, using the standard SBS sequencing reagent kit and the metrics were extracted using Illumina's sequencing analysis viewer. The sequencing analysis data showed that the sequencing metrics of the norbornene silanized substrate run are equivalent to those of substrates functionalized with acrylamides.

Figure 2A:
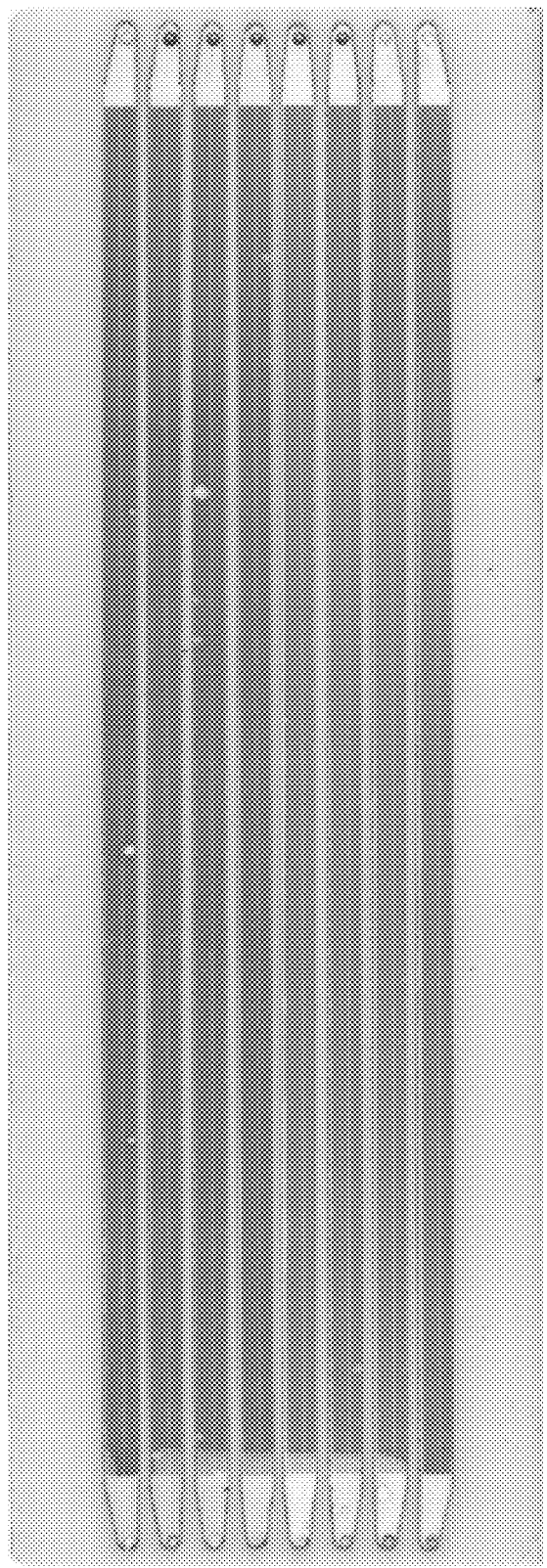
FIG. 2A shows a glass substrate patterned with nanowells silanized with the norbornene-silane derivative (1a) and subsequently coated and thermally cross-linked with PAZAM.
Figure 2B:
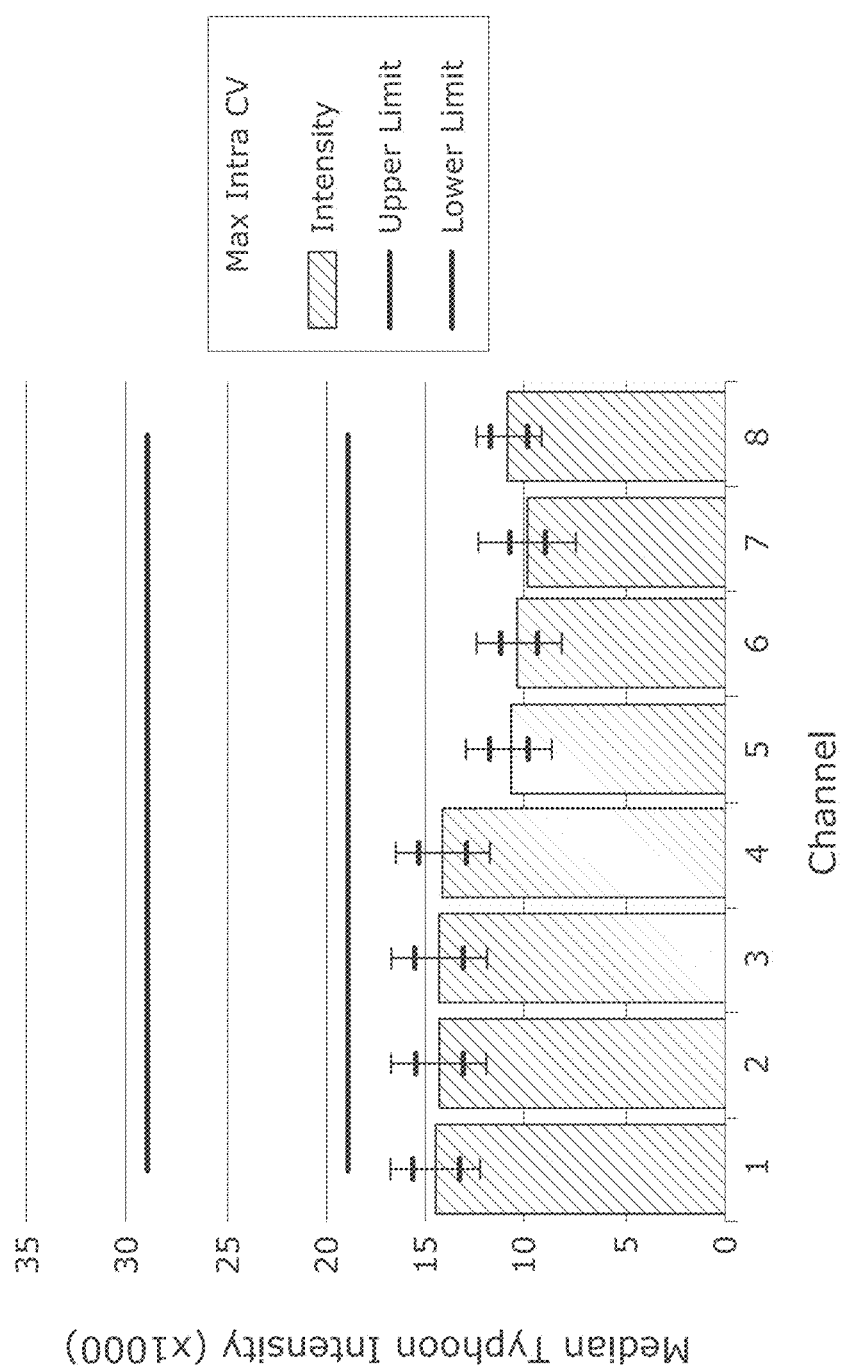
FIG. 2B shows the related chart of median fluorescence intensities of the grafted norbornene silane derivative (1a) silanized/PAZAM coated unpatterned surface hybridized with a complimentary TET dye-containing oligonucleotide sequence.

FIG. 2A shows a D263 Schott glass substrate patterned with nanowells silanized with the norbornene-silane derivative (1a) and subsequently coated and thermally cross-linked with PAZAM. The dark area is the actual fluorescence intensity observed after chemical mechanical polishing of the excess PAZAM and upon grafting P5/P7 primers and hybridizing with a TET-dye derivatized complementary strands. FIG. 2B shows the related chart of median fluorescence intensities for each lane of the same grafted norbornene (1a) silanized/PAZAM coated unpatterned surface hybridized with a complimentary TET dye-containing oligonucleotide sequence.

Figure 3A:
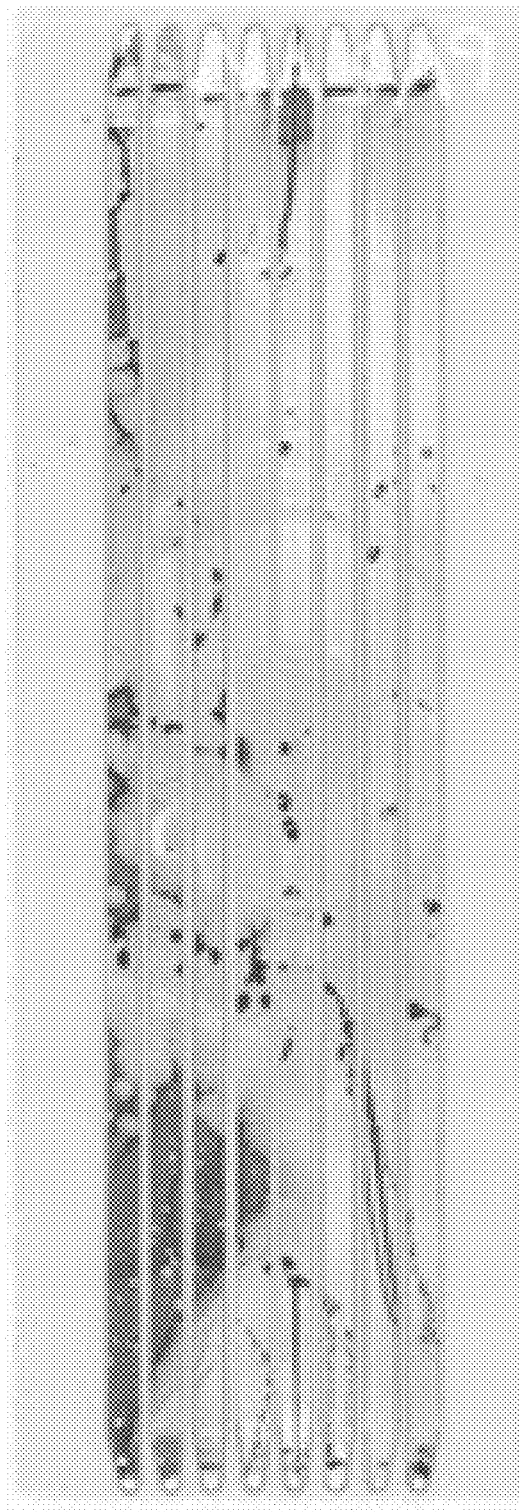
FIG. 3A shows a Typhoon fluorescence image of the grafted surface hybridized with a complimentary dye-containing oligonucleotide sequence using acrylamide functionalized substrate.
Figure 3B:
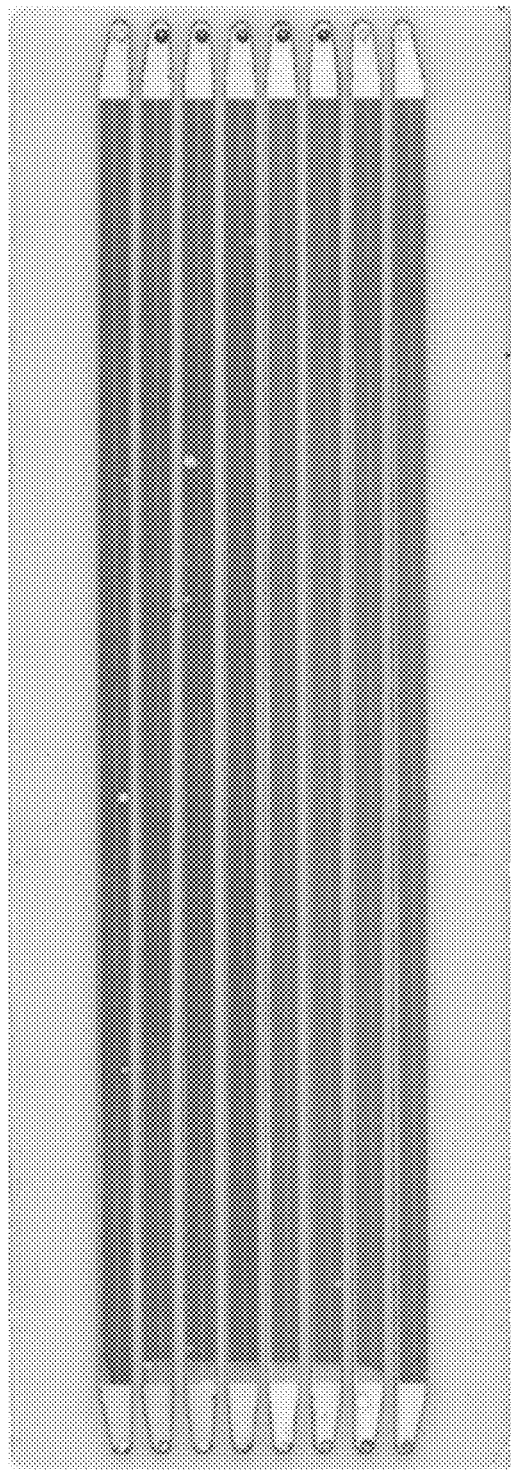
FIG. 3B shows a Typhoon fluorescence image of the grafted surface hybridized with a complimentary dye-containing oligonucleotide sequence using norbornene silane derivative (1a) silanized PAZAM coated substrate.
Figure 3C:
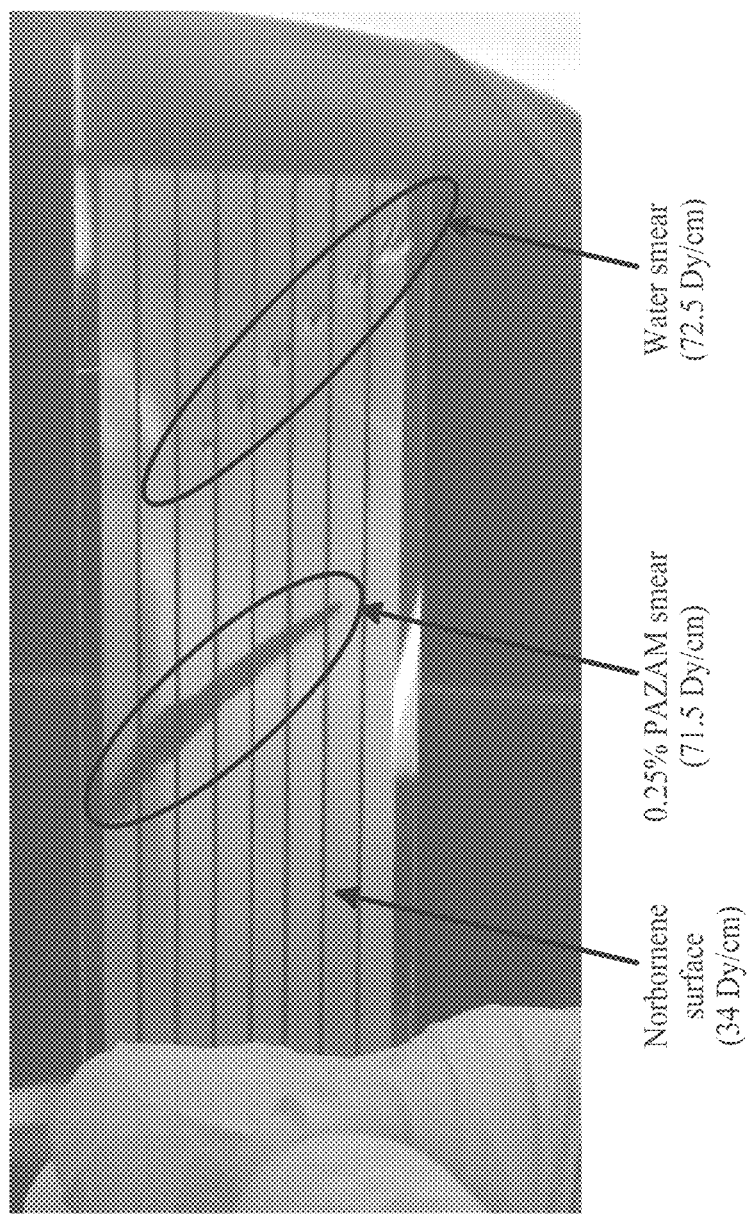
FIG. 3C shows that a 0.25% aqueous PAZAM solution wets a norbornene silane derivative (1a) silanized surface.

Not only did norbornene silanized substrate eliminate the need of additional cross-linking agent, norbornene silanized substrates displayed a preferential affinity for PAZAM and facilitated the spreading of aqueous PAZAM solution. As a result, the PAZAM coatings were more homogeneous and less sensitive to variations in substrate quality. FIG. 3A shows the typhoon image of a flow cell as a result of typical failure of spin coating using standard acrylamides functionalized surface. FIG. 3B shows the typhoon image of a norbornene silane derivative (1a) silanized flow cell, which results in more homogeneous coating. FIG. 3C shows that a 0.25% aqueous PAZAM solution wets a norbornene silane derivative (1a) silanized surface in comparison with water smears, even in the presence of a large energy mismatch between surface energies of the solid-liquid interface.

Example 3

Surface Stability Testing

Norbornene silanized/PAZAM coated substrates also demonstrated good shelf life. Several patterned substrates and unpatterned substrates were silanized with norbornene silane of Example 1 using YES method, then subject to PAZAM coating and crosslinking using the method described in Exampled 1 and 2. The patterned substrates were stored in a slide carrier in the dark at room temperature, inside a desiccator. After 30 days, these substrates were sequenced and provided acceptable TET QC results and seq-uencing metrics (FIG. 4).

Example 4

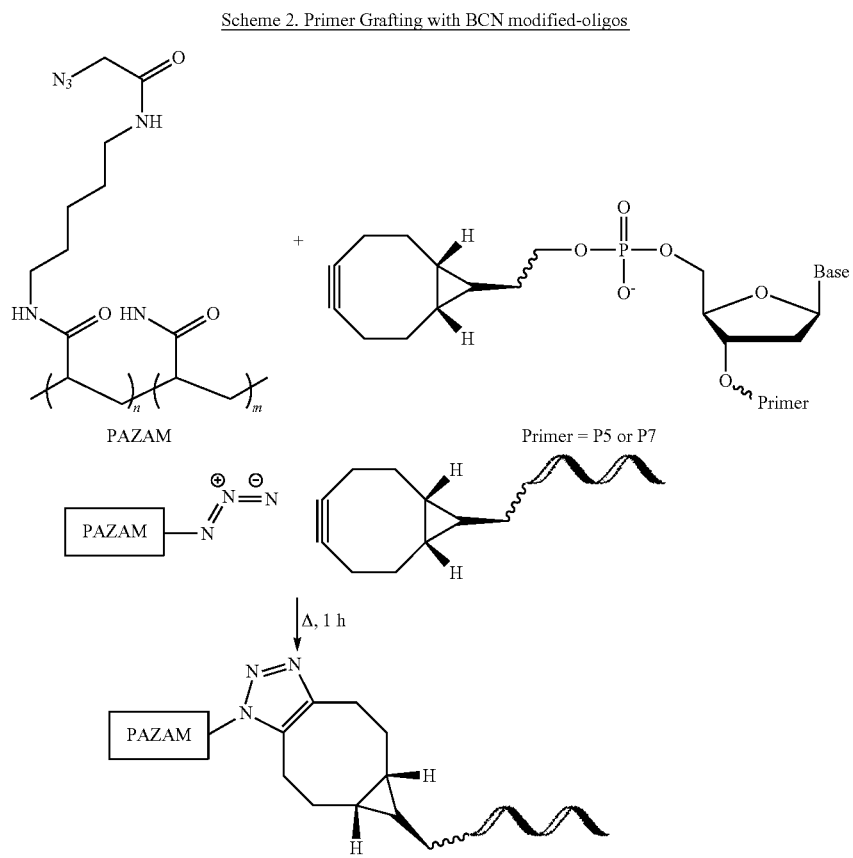

Scheme 2. Primer Grafting with BCN modified-oligos

One embodiment of a method for grafting BCN-modified oligos to a PAZAM-coated surface is as follows: 5'-modified BCN P5 and P7 oligos containing the same sequences as the standard P5 and P7 (thiophosphate and alkyne) oligos were used to react with a flow cell surface coated with PAZAM (0.25% w/v) without any catalysts (Scheme 2). The PAZAM coated surface was prepared by first treating the surface with 3-aminopropyltrimethoxysilane (APTMS), followed by treatment with acryloyl chloride (80 µL of neat acryloyl chloride and 40 µL of DIPEA in 1880 µL anhydrous MeCN) or activated acryloyl NHS ester (20 mg/mL in KPi pH=8.0, 200 mM) to form the unsaturated acrylamide groups. Then, PAZAM was introduced to the unsaturated surface and the substrate was incubated at 60° C. for 50-75 min (static). The general method is described in U.S. application Ser. No. 13/784,368, which is hereby incorporated by reference in its entirety. The detailed experimental conditions for each lane of the flow cell are illustrated in Table 1 below.

TABLE 1

| Details | Total [alkyne]/uM |
|---|---|
| 1% PAZAM, standard Blackpool grafting | 2 |
| 1% PAZAM, standard Blackpool grafting | 2 |
| 1% PAZAM, Copper-free grafting, P5 and P7 BCN primers | 2 |
| 1% PAZAM, Copper-free grafting, P5 and P7 BCN primers | 2 |
| 1% PAZAM, Copper-free grafting, P5 and P7 BCN primers | 2 |
| 1% PAZAM, Copper-free grafting, P5 and P7 BCN primers | 2 |

TABLE 1-continued

| Details | Total [alkyne]/uM |
|---|---|
| 1% PAZAM, Copper-free grafting, P5 BCN primer only | 2 |
| 1% PAZAM, Copper-free grafting, P7 BCN primer only | 2 |

Figure 5A:
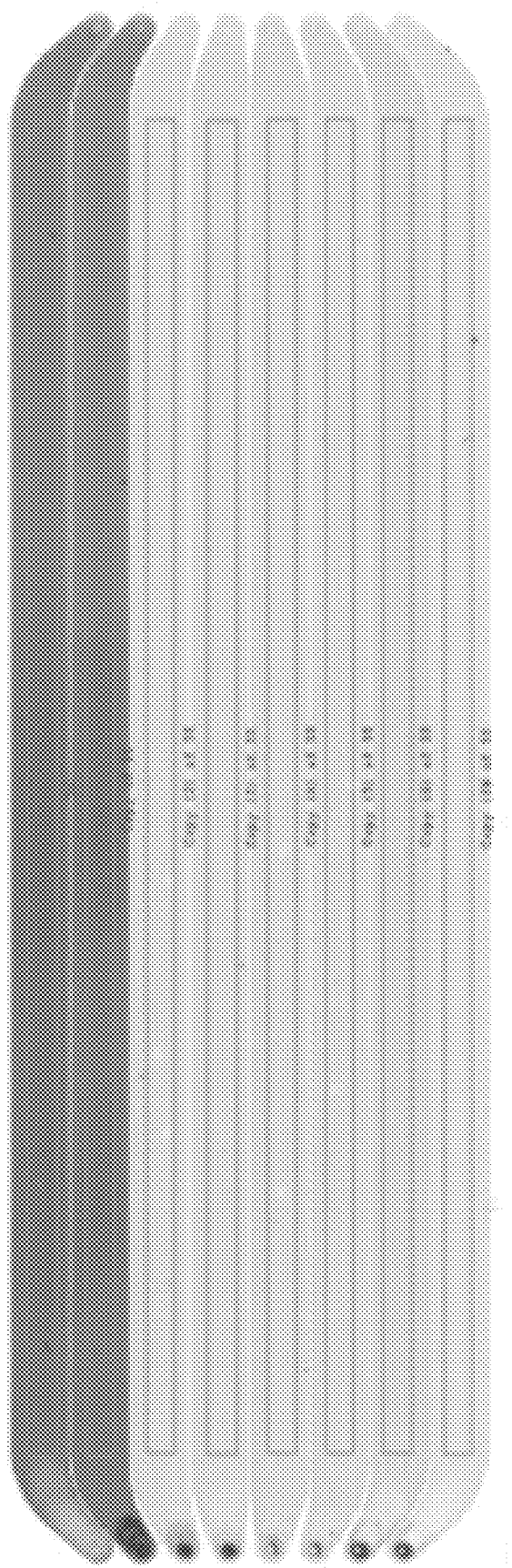
FIG. 5A shows an initial Typhoon image of the grafted surface of a substrate using a copper-free grafting method with BCN modified primers.
Figure 5B:
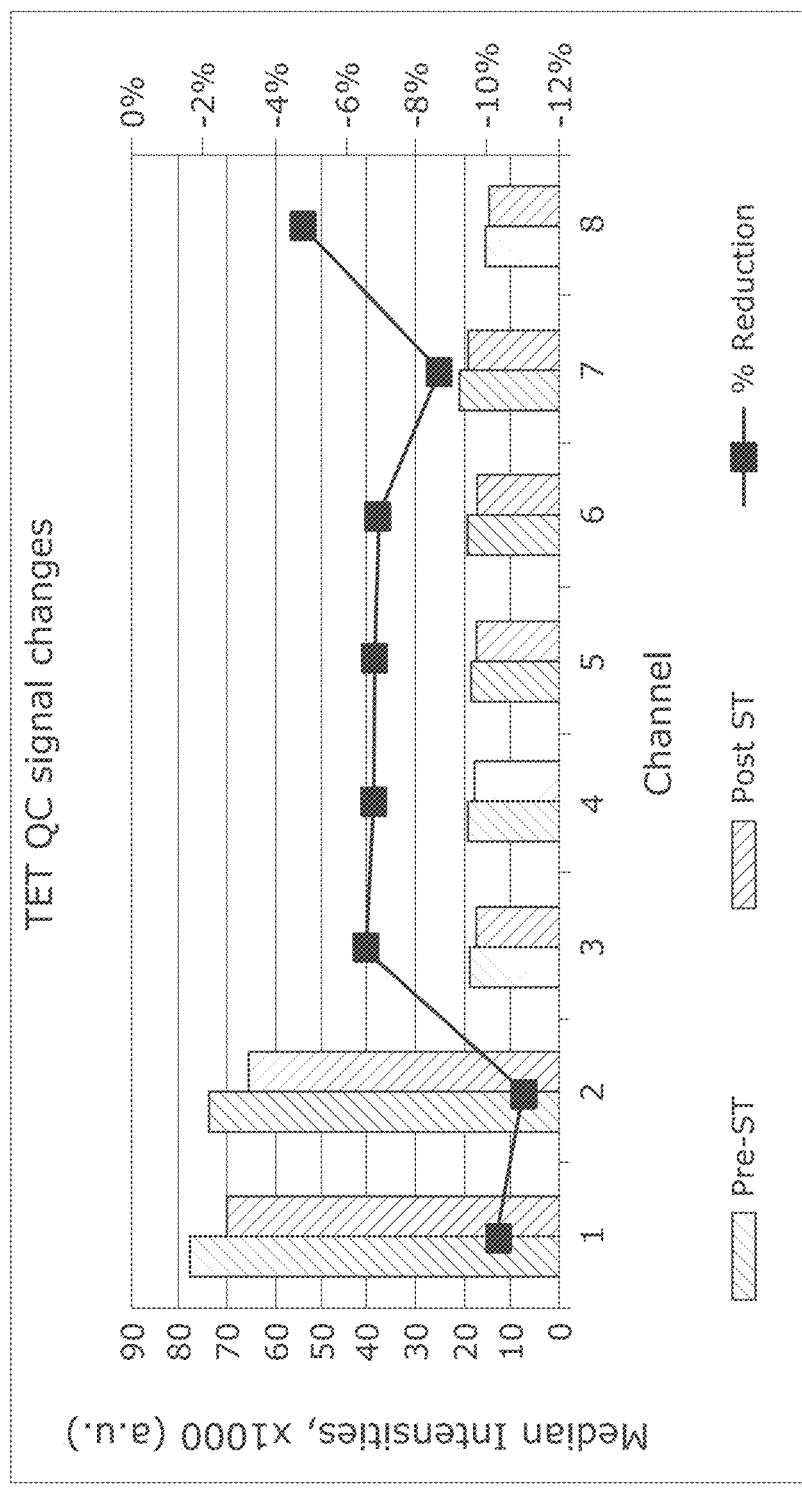
FIG. 5B is a line and bar chart that illustrates the initial TET QC data after grafting a PAZAM surface with BCN modified primers and surface loss percentage as measured after a thermal Stress Test.

An initial Typhoon image of the grafted surface of the flow cell using the catalyst-free grafting of BCN modified oligos described above is depicted in FIG. 5A. The flow cell surface was subjected to a thermal Stress test to determine the robustness of the grafted coating and the result shown in FIG. 5B demonstrated that the signal reduction (approximately correlated with surface loss) is minimal and consistent with the standard lanes.

Figure 6A:
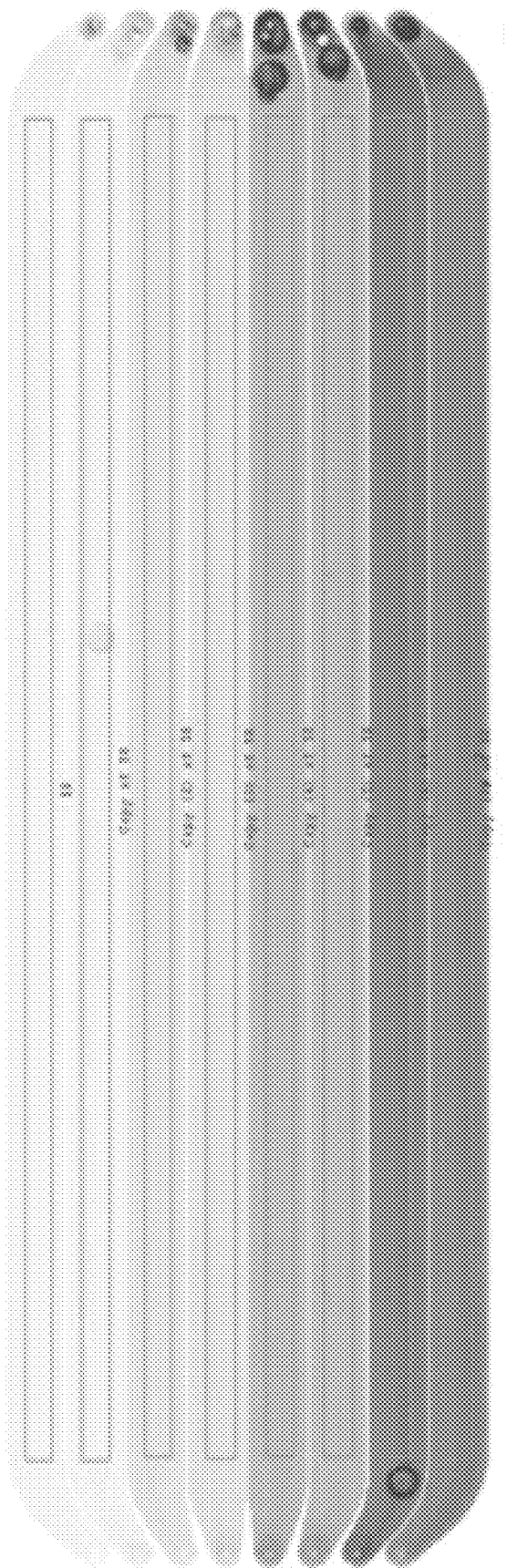
FIG. 6A shows an initial Typhoon image of the grafted surface of a substrate using copper-free grafting method and different concentrations of BCN modified primers.
Figure 6B:
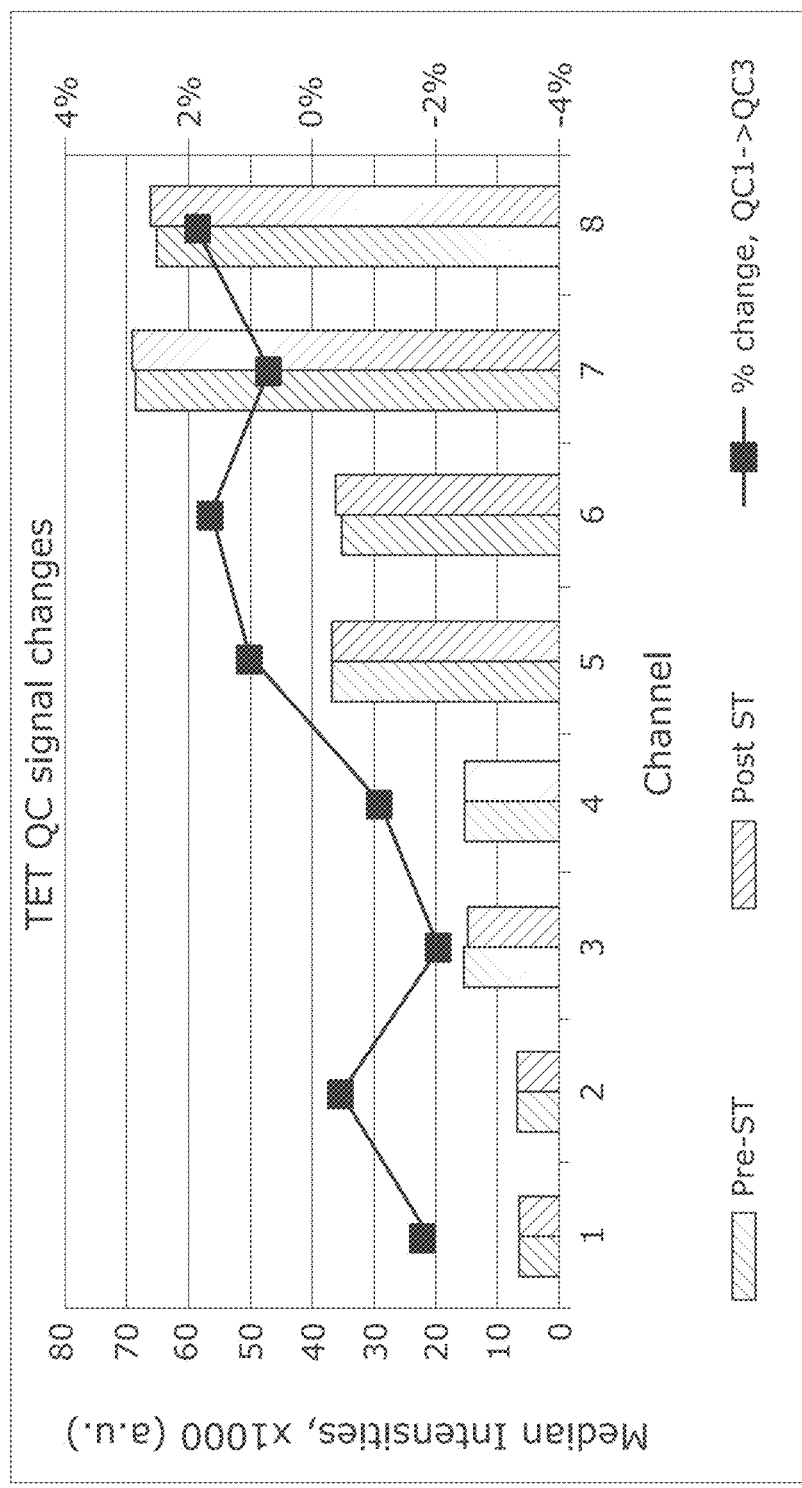
FIG. 6B is a line and bar chart that illustrates the initial TET QC data after grafting a PAZAM surface with different concentrations of BCN modified primers and surface loss percentage as measured after a thermal Stress Test.

To explore the experimental condition for obtaining optimal primer densities, different concentrations of BCN modified oligos were also tested (Table 2). The PAZAM coated flow cell surface was prepared from a norbornene modified silane using the similar procedure described in Example 1. Then, different concentrations of BCN modified primers were grafted to the polymer layer. The initial Typhoon image of the grafted surface of a flow cell using copper-free grafting method and different concentrations of BCN primers is demonstrated in FIG. 6A. The flow cell surface was also subjected to a thermal Stress test and FIG. 6B indicates the results from TET QC analyses performed before and after surface thermal stressing.

TABLE 2

| Channel | Details | Total [alkyne]/uM |
|---|---|---|
| 1 | 0.25% PAZAM, Copper-free grafting using P5 and P7 BCN primers | 2 |
| 2 | | 2 |
| 3 | | 4 |
| 4 | | 4 |
| 5 | | 10 |
| 6 | | 10 |
| 7 | | 20 |
| 8 | | 20 |

Figure 7A:
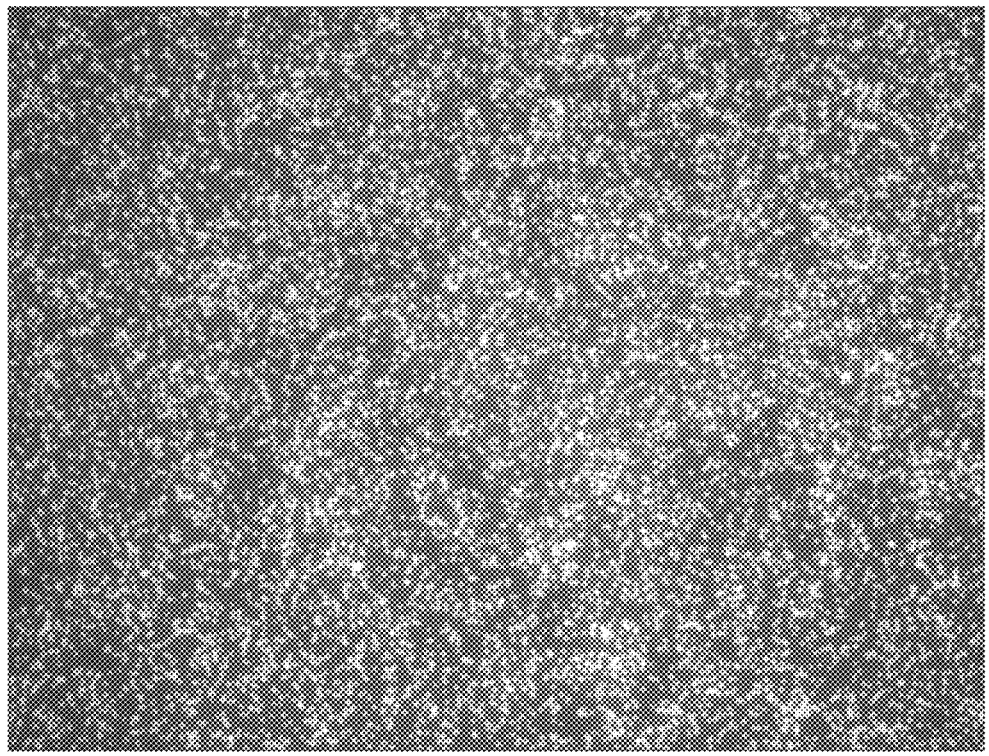
FIG. 7A shows a fluorescence image of clusters grown from a BCN modified primer grafted surface with low cluster density.
Figure 7B:
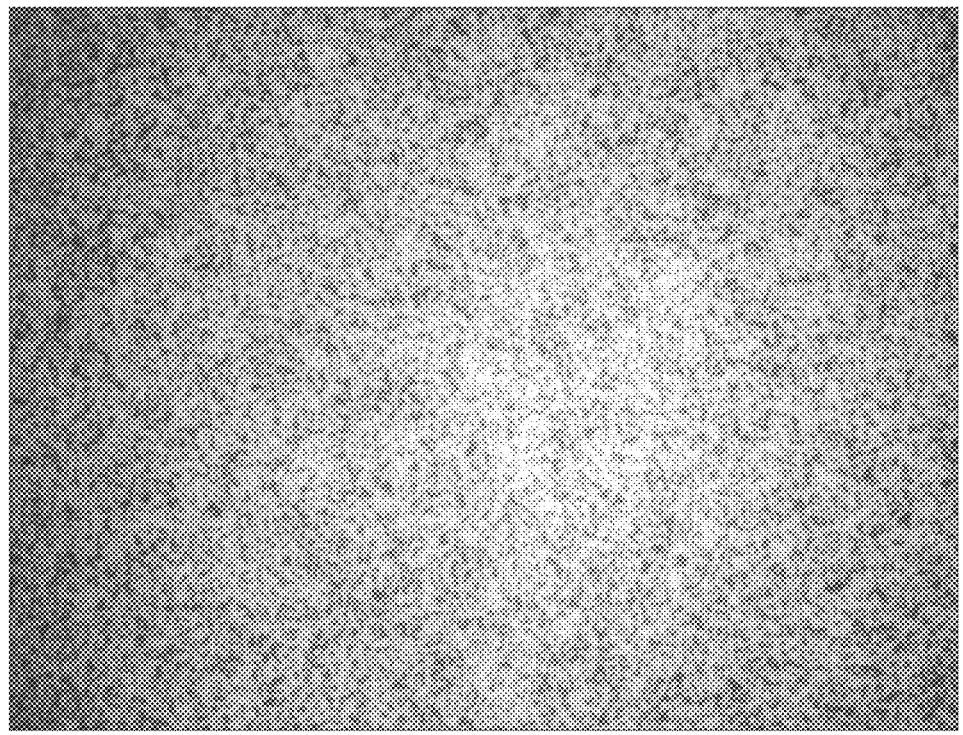
FIG. 7B shows a fluorescence image of clusters grown from a BCN modified primer grafted surface with high cluster density.

Bridge amplification performed on both grafted flow cell surfaces proceeded smoothly. The clusters were viewed using a fluorescence microscope, and they appeared comparable with those grown in the control lanes. FIG. 7A shows a fluorescence image of clusters grown from a BCN primer grafted surface. The template seeding concentration was 0.5 µM. Similarly, FIG. 7B shows fluorescence images of clusters grown from a BCN primer grafted surface where the template concentration was 3 µM.

The BCN modified oligos-grafted flow cell surfaces were then taken through several sequencing runs using a HiSeq instrument. The high level metrics were comparable with the control lanes. Comparison of the SBS data shows that the high-level sequencing metrics are very comparable with results currently obtained from PAZAM surfaces grafted using standard alkyne oligos.

Example 5

Primer Grafting with BCN-Oligos

In some embodiments of the substrate surface preparation processes described herein, the raw substrates are first coated with a silane derivative, e.g., norbornene derivatized silane, then PAZAM is spin coated on to the surface. The substrate is then polished and assembled, subsequently subjected to primer grafting and QC. The alternative approach of preparing substrate using pre-grafted PAZAM by functionalizing PAZAM with the standard P5 and P7 oligos in solution was also explored. This process offers several important advantages. Moving the primer grafting step upstream would allow for more effective polymer purification and greater control of the amount of oligos used to achieve a target surface primer density. In addition, the workflow to a finished substrate can be shortened as the coated substrate surface would already contain the primers required for template hybridization and thus removing the need to use specialized fluidic instrumentation to achieve adequately grafted surfaces.

Figure 11:
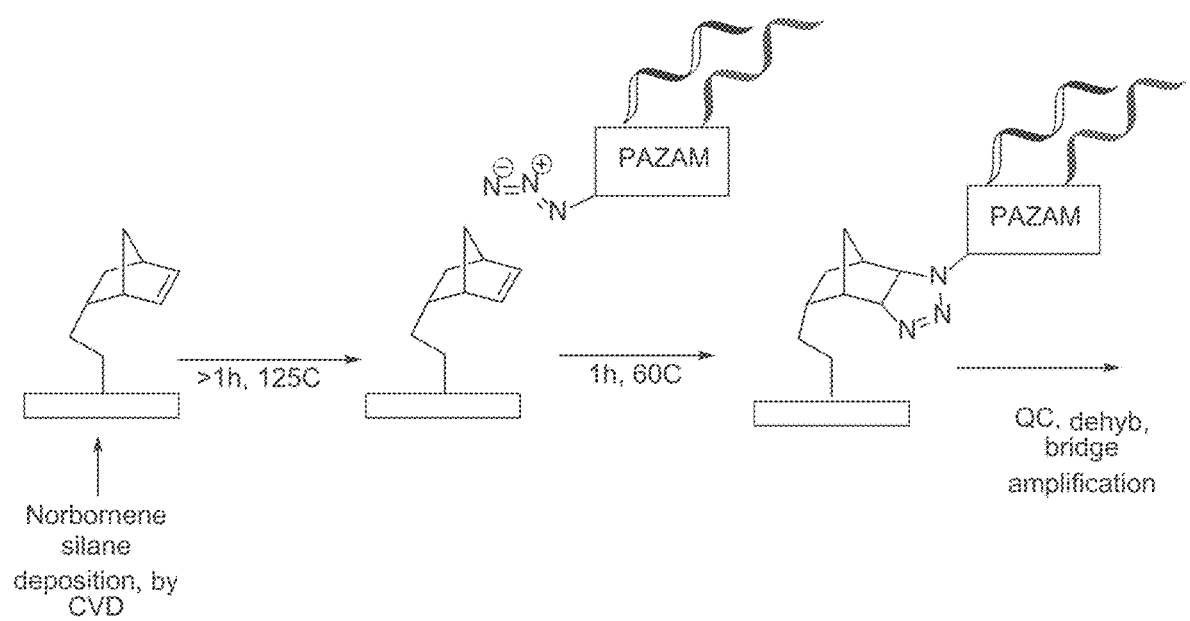
FIG. 11 illustrates a process of coating a flow cell surface pre-treated with a norbornene-derivatized silane layer.

A solution of the mixed P5/P7 BCN modified primers (total concentration=15 µM) was added to an aqueous solution of PAZAM (0.5 w/v %) and the resulting mixture was heated for 2 hours at 70° C. After cooling to room temperature, the mixture was used to coat a standard HiSeq flow cell, pre-treated with a norbornene-derivatized silane layer (FIG. 11).

Figure 8A:
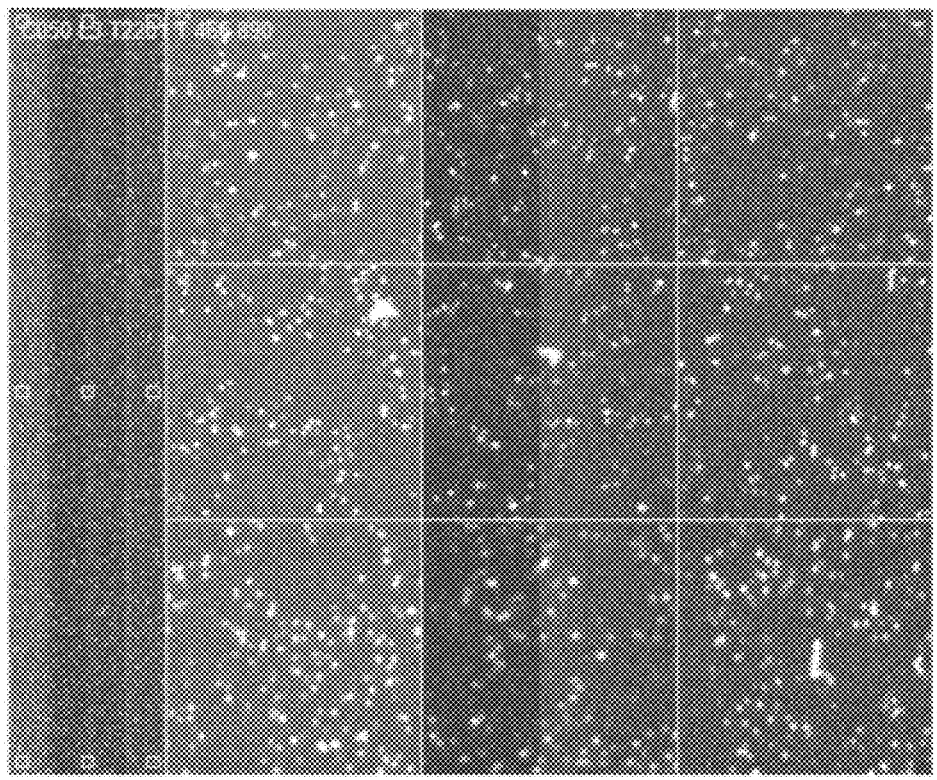
FIGS. 8A and 8B shows a thumbnail image of clusters from both surfaces of a channel coated with a pre-conjugated PAZAM mixture obtained from a standard HiSeq system.
Figure 8B:
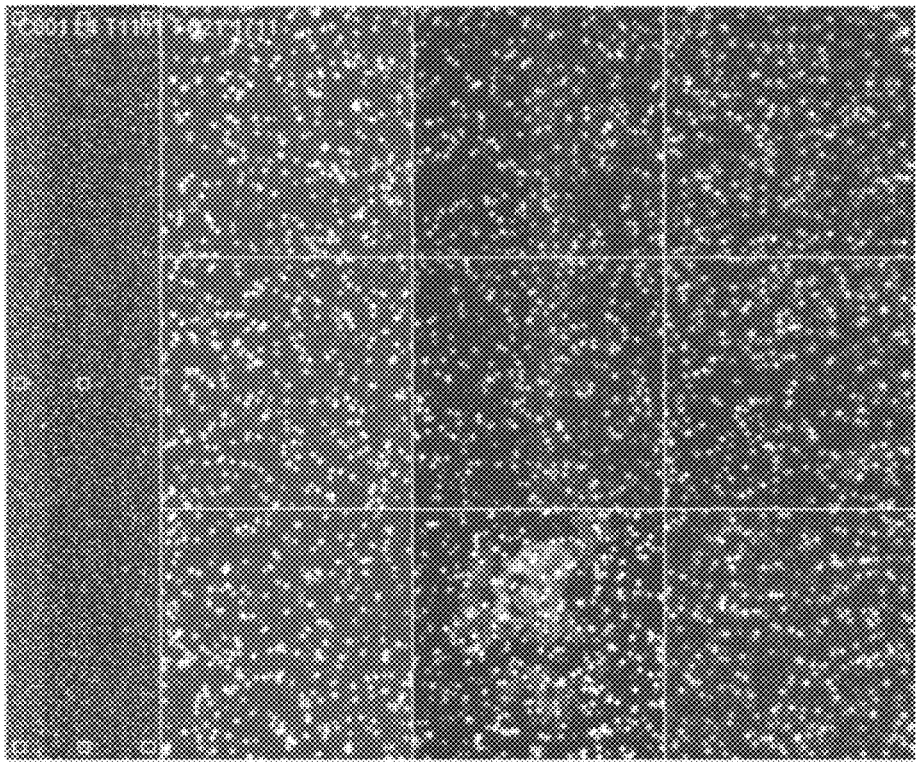

The pre-grafted surface was subjected to the standard thermal stress test and the signal losses (corresponding to surface losses) were comparable to the control. A 2×26 HiSeq SBS sequencing experiment was performed using the standard reagents as described in Illumina standard protocol. FIG. 8A shows the type of clusters obtained from a pre-grafted PAZAM surface. The seeding template concentration was reduced (0.5 µM). In FIG. 8B, the bottom surface from a channel in the same flow cell is shown with the seeding concentration increased to 3 µM. The change in cluster density is within expected limits and therefore shows that this new surface behaves very similarly to control surfaces. Inspection of the images (FIGS. 8A and 8B) indicated that the clusters were typical with the only variation being the apparent cluster "size" as estimated by consideration of the Full Width Half Max (FWHM), which is used internally as a proxy for the apparent cluster size. This is consistent with the reduced intensity of these clusters. A comparison between the SBS metrics for the pre-grafted, control and BCN modified primer-grafted channels confirms that SBS cycles were proceeding from the clusters generated on the surface.

Figure 9:
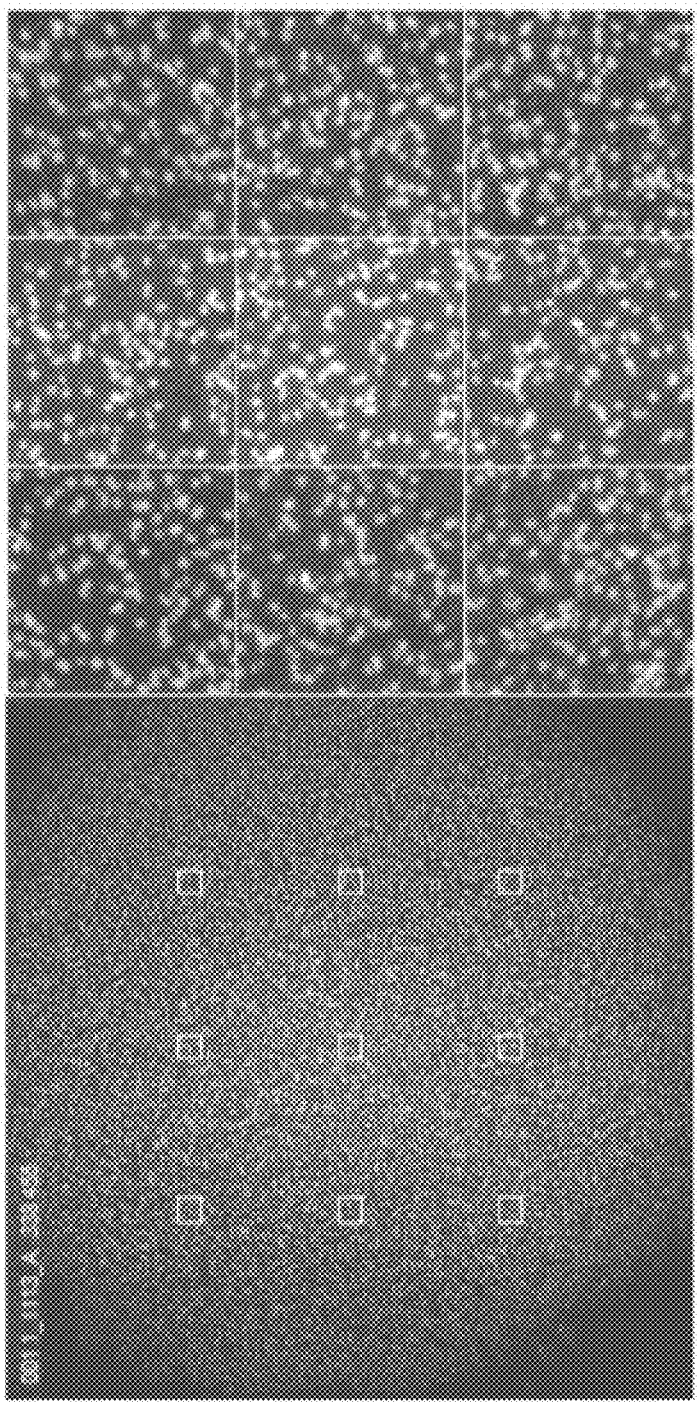
FIG. 9 shows a thumbnail image of clusters from one surface of a channel coated with pre-conjugated PAZAM mixture obtained from a standard MiSeq system.

A similar, longer SBS run was performed using a MiSeq instrument. In this case, a standard PAZAM solution was incubated with the BCN-modified primers for 3 hours at 70° C. The resulting grafted polymer mixture was then applied to a norbornene functionalized MiSeq flow cells following the standard protocols. On-board cluster generation was followed by a 2×151 cycle SBS run performed using a standard four-channel system. FIG. 9 shows a thumbnail image of clusters grown from a channel surface coated with pre-conjugated PAZAM mixture obtained from a standard MiSeq system (2×151 SBS). The right portion of the image is a magnification of the left portion of the image.

The SBS images for all cycles from this run are comparable with those from standard (SFA and PAZAM) SBS experiments. The signal-to-noise measurements are also very similar compared against standard surfaces, showing that the no obvious entrapment of dye molecules takes place during sequencing (i.e. the polymer coating does not appear to undergo additional changes).

What is claimed is:

1. A method of preparing a first surface of a substrate, the method comprising:
    providing a substrate having a first surface comprising surface-bound silane or silane derivative, wherein the silane or silane derivative comprises a first plurality of unsaturated moieties selected from the group consisting of norbornene, heteronorbornene, norbornene derivatives, and optionally substituted variants and combinations thereof, and wherein the first plurality of unsaturated moieties are covalently attached to the silane or silane derivative, optionally through linkers;
    covalently attaching a functionalized molecule comprising functional groups to the silane or silane derivative by reacting the functional groups of said functionalized molecule with the first plurality of unsaturated moieties to form a coating layer;
    contacting oligonucleotides comprising a second plurality of unsaturated moieties with the functionalized molecule, wherein the second plurality of unsaturated moieties are selected from the group consisting of cycloalkenes, cycloalkynes, heterocycloalkenes, heterocycloalkynes, alkynes, and optionally substituted variants and combinations thereof;
    reacting the second plurality of unsaturated moieties of the oligonucleotides with the functional groups of the functionalized molecule to form covalent bonding, wherein the functionalized molecule comprises poly (N-(5-azidoacetamidylpentyl) acrylamide-co-acrylamide) (PAZAM).

2. The method of claim 1, wherein the first plurality of unsaturated moieties of the silane or silane derivative are optionally substituted norbornene.

3. The method of claim 1, wherein the second plurality of unsaturated moieties of the oligonucleotides are selected from the group consisting of alkynes, cyclooctyne, bicycloalkynes, and optionally substituted variants and combinations thereof.

4. The method of claim 3, wherein the second plurality of unsaturated moieties of the oligonucleotides are selected from the group consisting of optionally substituted cyclooctyne, optionally substituted bicyclononyne, and optionally substituted bicyclo[6.1.0]non-4-yne.

5. The method of claim 3, wherein the second plurality of unsaturated moieties is an optionally substituted alkyne.

6. The method of claim 1, wherein the silane or silane derivative are applied to the first surface of the substrate by chemical vapor deposition or liquid deposition.

7. The method of claim 1, wherein the first surface is patterned with nanowells silanized with the silane or silane derivative.

8. The method of claim 1, wherein the linkers are present, and wherein the linkers are covalently attached between silicon atoms of the silane or silane derivative and the first plurality of unsaturated moieties.

9. The method of claim 8, wherein the linkers are selected from the group consisting of optionally substituted alkylenes, optionally substituted heteroalkylenes, optionally substituted cycloalkylenes, optionally substituted heterocyclylenes, optionally substituted arylenes, optionally substituted heteroarylenes, optionally substituted polyethylene glycols, cleavable linkers, and combinations thereof.

10. The method of claim 9, wherein the linkers are selected from the group consisting of optionally substituted alkylenes.

11. The method of claim 2, wherein the linkers are present, and wherein the linkers are covalently attached between silicon atoms of the silane or silane derivative and the norbornene moieties, and wherein the surface bound silane or silane derivative comprises the formula:

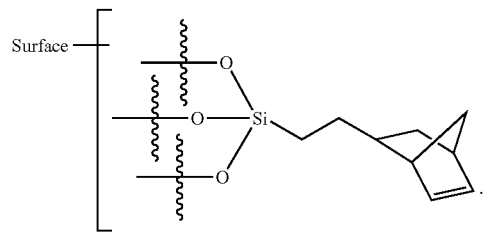

12. The method of claim 11, wherein the surface-bound silane or silane derivative is prepared by reacting the compound:

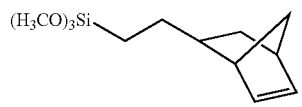

with the first surface of the substrate.

13. The method of claim 11, wherein the second plurality of unsaturated moieties is optionally substituted alkyne.

14. The method of claim 11, wherein the second plurality of unsaturated moieties is optionally substituted bicyclo[6.1.0]non-4-yne.

15. The method of claim 1, wherein the substrate comprises glass.

16. The method of claim 1, wherein the first surface of the substrate comprises both functionalized molecules coated regions and inert regions.

17. The method of claim 11, wherein the substrate comprises glass.

18. The method of claim 11, wherein the first surface of the substrate comprises both functionalized molecules coated regions and inert regions.

* * * * *